United States Patent
Greer et al.

(10) Patent No.: US 8,560,118 B2
(45) Date of Patent: Oct. 15, 2013

(54) METHODS, DEVICES, AND SYSTEMS FOR NON-MECHANICALLY RESTRICTING AND/OR PROGRAMMING MOVEMENT OF A TOOL OF A MANIPULATOR ALONG A SINGLE AXIS

(75) Inventors: Alexander Greer, Calgary (CA); Garnette Sutherland, Calgary (CA); Tim Fielding, Brampton (CA); Perry Newhook, Caledon (CA)

(73) Assignee: NeuroArm Surgical Ltd., Calgary (CA)

( * ) Notice: Subject to any disclaimer, the term of this patent is extended or adjusted under 35 U.S.C. 154(b) by 768 days.

(21) Appl. No.: 12/596,426

(22) PCT Filed: Apr. 16, 2008

(86) PCT No.: PCT/IB2008/003323
§ 371 (c)(1),
(2), (4) Date: Mar. 23, 2010

(87) PCT Pub. No.: WO2009/037576
PCT Pub. Date: Mar. 26, 2009

(65) Prior Publication Data
US 2010/0198402 A1    Aug. 5, 2010

Related U.S. Application Data

(60) Provisional application No. 60/912,146, filed on Apr. 16, 2007.

(51) Int. Cl.
*B25J 3/00* (2006.01)
*B25J 13/00* (2006.01)
*G06G 7/62* (2006.01)

(52) U.S. Cl.
USPC ............... 700/247; 700/257; 703/6; 901/41; 901/49

(58) Field of Classification Search
USPC ........... 606/139; 600/245; 382/131; 700/247, 700/257, 250; 703/1, 6; 901/41, 49
See application file for complete search history.

(56) References Cited

U.S. PATENT DOCUMENTS

| | | | |
|---|---|---|---|
| 5,046,022 A | * | 9/1991 | Conway et al. ............. 700/250 |
| 5,078,140 A | | 1/1992 | Kwoh ........................ 176/253 |

(Continued)

FOREIGN PATENT DOCUMENTS

| | | |
|---|---|---|
| EP | 1 103 229 | 5/2001 |
| WO | WO 00/51486 | 9/2000 |
| WO | WO 01/62173 | 8/2001 |

OTHER PUBLICATIONS

International Preliminary Report on Patentability issued in International Application No. PCT/IB2008/003323, dated Jan. 5, 2010.

(Continued)

*Primary Examiner* — Ronnie Mancho
(74) *Attorney, Agent, or Firm* — Fulbright & Jaworki LLP

(57) ABSTRACT

Methods, devices (such as computer readable media), and systems (such as computer systems) for performing movements of a tool of a medical robot along a single axis that are achieved by electronically limiting the medical robot's movement to produce movement of the tool along the single axis rather than mechanically restricting the medical robot's movement to produce the single axis movement. The tool's movement will be along the single axis even if a user is moving an input device linked to the medical robot in other axes during the single axis movement. In addition, techniques are disclosed for automating the single axis movement such that it can be programmed to stop at a target location and start at or near a second (e.g., starting) location, which is useful for a procedure such as a brain biopsy, breast biopsy or implantation, and such that a user can execute a command instructing the medical robot to perform the movement without the need for the user to manipulate an input device to cause real-time responsive movement of the medical robot.

15 Claims, 21 Drawing Sheets

(56) References Cited

U.S. PATENT DOCUMENTS

| | | | |
|---|---|---|---|
| 5,445,166 A | 8/1995 | Taylor | 128/897 |
| 5,572,999 A | 11/1996 | Funda et al. | 600/118 |
| 5,762,458 A | 6/1998 | Wang et al. | 414/1 |
| 6,006,127 A | 12/1999 | Van Der Brug et al. | 600/427 |
| 6,013,087 A | 1/2000 | Adams et al. | 606/130 |
| 6,120,433 A | 9/2000 | Mizuno et al. | 600/102 |
| 6,547,782 B1 | 4/2003 | Taylor | 606/14 |
| 6,671,538 B1 * | 12/2003 | Ehnholm et al. | 600/425 |
| 7,025,761 B2 | 4/2006 | Wang et al. | 606/1 |
| 7,074,179 B2 | 7/2006 | Wang et al. | 600/101 |
| 7,121,781 B2 | 10/2006 | Sanchez | 414/1 |
| 7,155,316 B2 | 12/2006 | Sutherland et al. | 700/248 |
| 2003/0055410 A1 * | 3/2003 | Evans et al. | 606/1 |
| 2003/0060809 A1 | 3/2003 | Wang et al. | 606/1 |
| 2003/0109780 A1 | 6/2003 | Coste-Maniere et al. | 600/407 |
| 2004/0253079 A1 | 12/2004 | Sanchez | 414/1 |
| 2010/0063630 A1 * | 3/2010 | Sutherland et al. | 700/264 |

OTHER PUBLICATIONS

International Search Report issued in International Application No. PCT/IB2008/003323, dated Feb. 4, 2010.

Written Opinion issued in International Application No. PCT/IB2008/003323, dated Jun. 4, 2009.

Hayashibe, et al., "Robotic surgery setup simulation with the integration of inverse-kinematics computation and medical imaging", *Computer Methods and Programs in Biomedicine*, 83(1): 63-72, 2006.

* cited by examiner

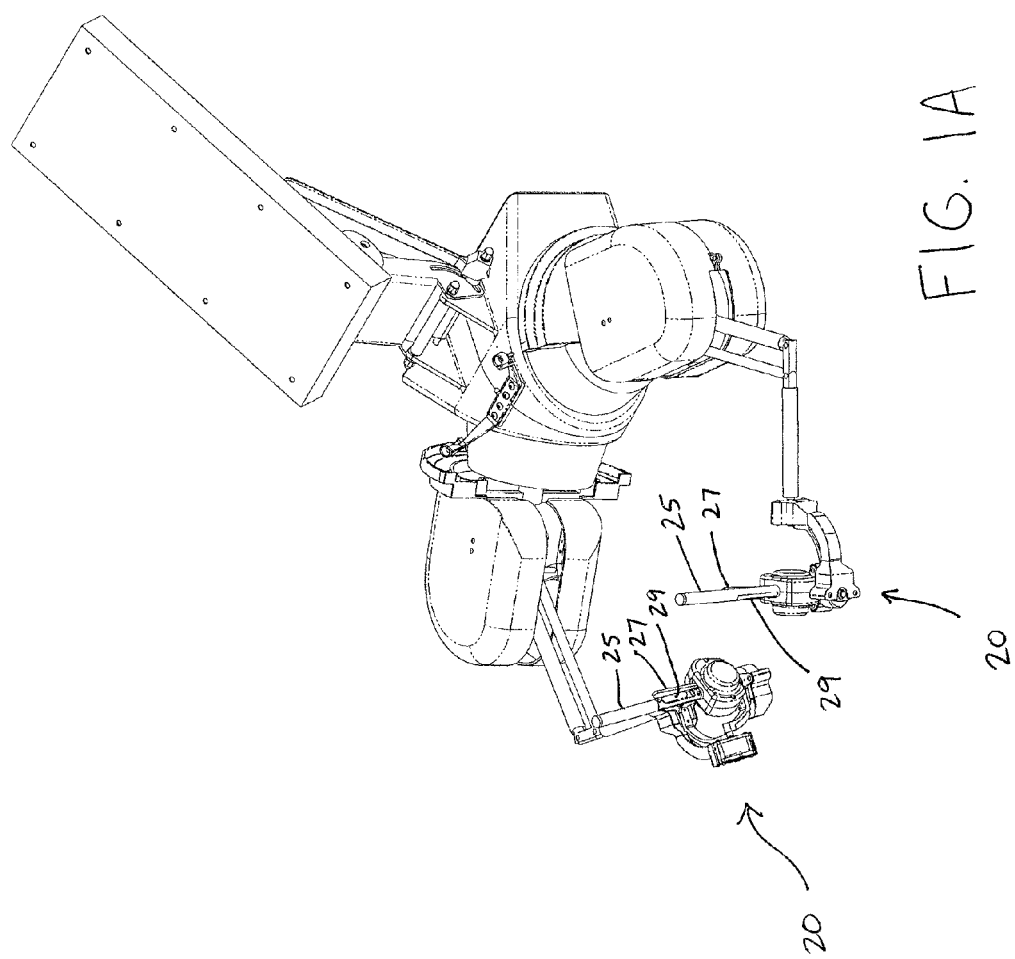

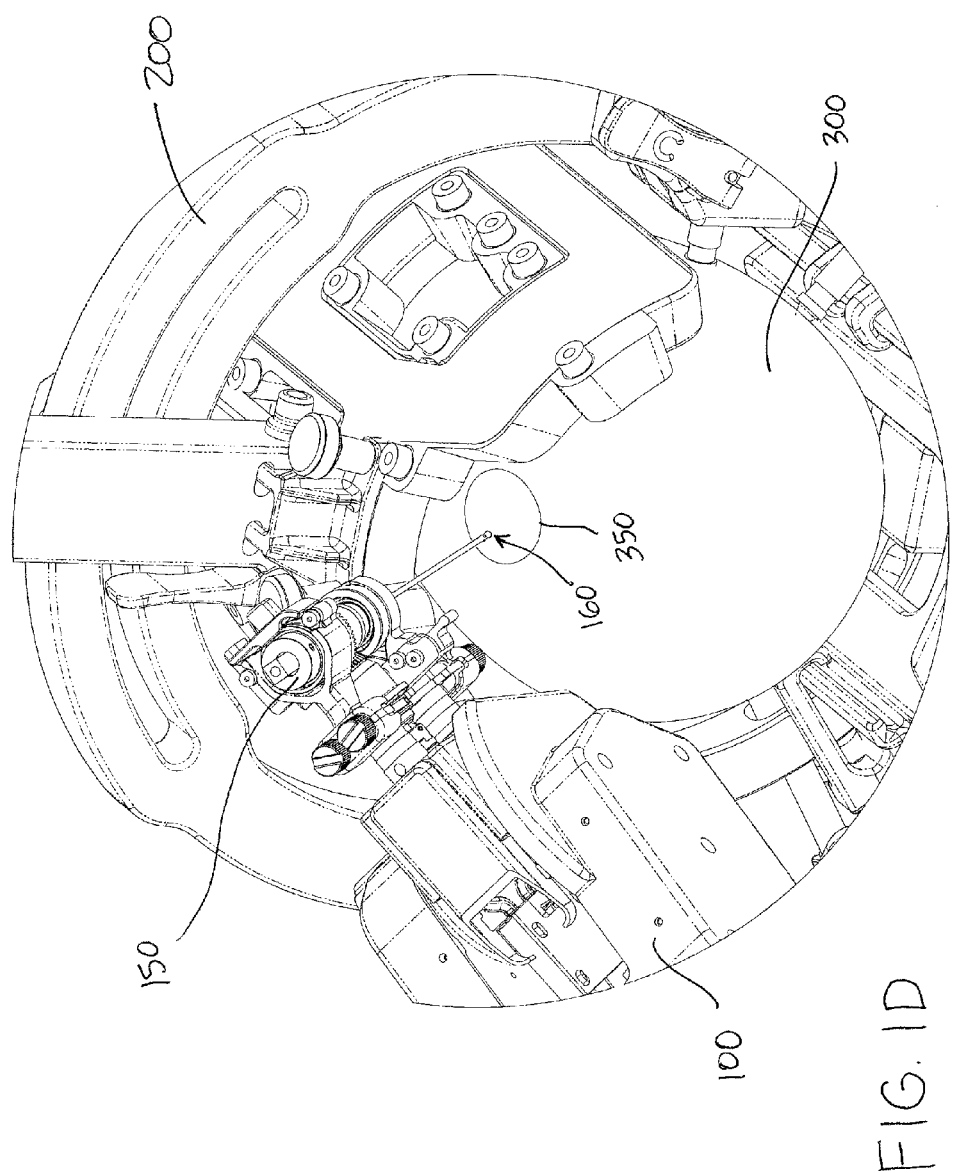

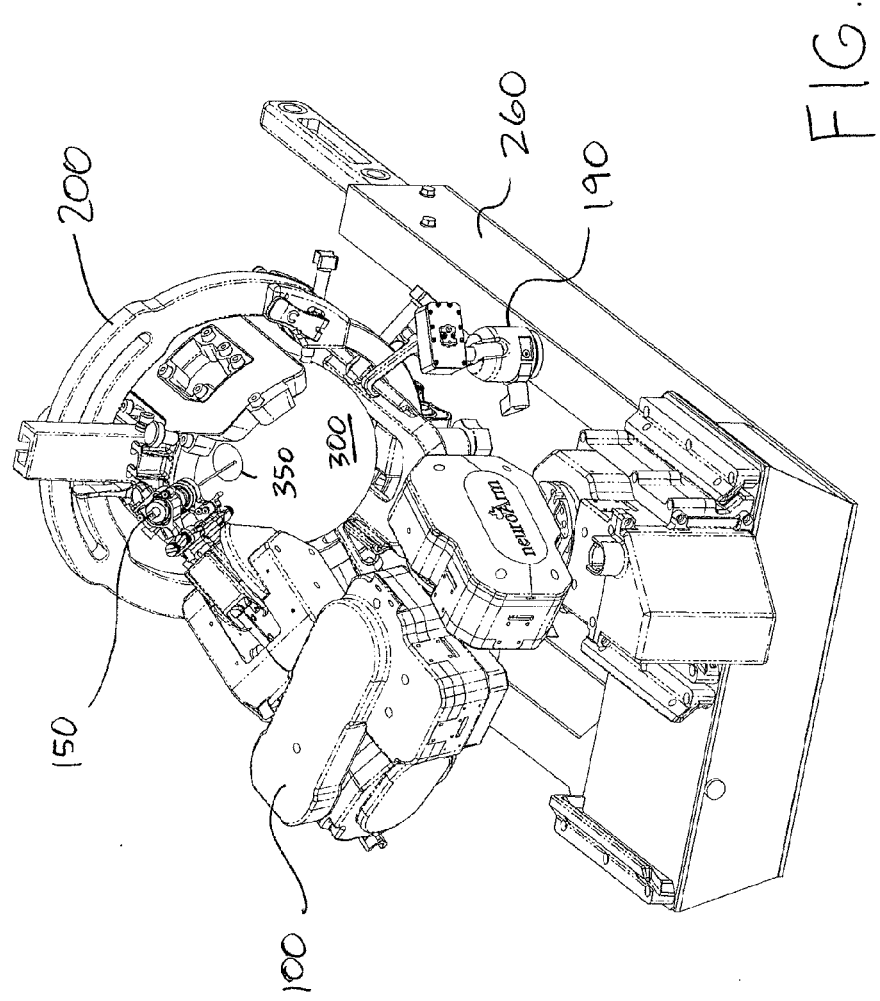

METHODS, DEVICES, AND SYSTEMS FOR NON-MECHANICALLY RESTRICTING AND/OR PROGRAMMING MOVEMENT OF A TOOL OF A MANIPULATOR ALONG A SINGLE AXIS

CROSS REFERENCE TO RELATED APPLICATIONS

This application is a national phase application under 35 U.S.C. §371 of International Application No. PCT/IB2008/003323, filed Apr. 16, 2008, which claims priority to U.S. Provisional Patent Application Ser. No. 60/912,146, filed Apr. 16, 2007, the entire contents of each of which are incorporated by reference. Co-pending U.S. patent application Ser. No. 12/596,418 is also incorporated by reference.

BACKGROUND INFORMATION

The present methods, devices, and systems relate generally to the field of surgical robotics, and more particularly to the non-mechanical restriction of a manipulator (e.g., a robotic arm with multiple degrees of freedom) to movement of a tool by the manipulator along a single axis. An example of a procedure that can be carried out according to the present methods, devices, and systems is an automated biopsy. An example of a surgical robot that can be used in a procedure to which the present methods, devices, and systems relate is disclosed in U.S. Pat. No. 7,155,316 (the "'316 patent"), which is incorporated by reference.

In order to perform stereotactic procedures (e.g., take a needle or small tool and hit a target within a three dimensional space) it is advantageous to limit the extent to which the tool can deviate from its planned trajectory. Therefore, in order to use a robot to perform stereotactic procedures using a master-slave interface, it can be desirable to nullify any inputs to the master controllers in the X and Y coordinates thus restricting movement at the tool tip to the Z axis.

Current procedures using frame-based or frameless stereotactic tools create Z-lock conditions through mechanical limitations. The most common process for stereotactic procedures (frame-based) requires the fixture of a rigid head frame to the patient's head. This frame serves as a mechanical means of guiding stereotactic tools through pre-planned paths by mechanically limiting X and Y axis movement. Other frameless stereotactic tools that use mechanical arms or tool attachments execute stereotactic procedures by fixing the patient's head in space, positioning the mechanical arm in a pre-planned path position, and mechanically locking the degrees of freedom associated with the arm. The result is a mechanical Z-lock along a pre-planned path.

In both the frame-based and frameless stereotactic procedures, the pre-planned path is derived from an image taken hours before the procedure. However, the brain is not fixed within the cranial cavity and can shift as a result of damage, tumours, hydration, and body position changes. These relatively small brain shifts can be problematic in term of accuracy and pose a safety concern. As a result, post surgical images and other tools are used to ensure accurate and safe procedures with existing tools. Furthermore, in frame-based stereotactic procedures, attachment of a head frame to the patient's head is also required; this is both uncomfortable and time consuming.

Significant time is associated with pre-operative planning and post-surgical imaging. Moreover, frameless stereotaxy navigation systems require line of sight with the patient's head and the surgeon's tools. This can pose a problem for surgeons who need to be positioned by the head of the patient to navigate stereotactic tools to the target.

SUMMARY

Embodiments of the present methods and systems enable a user, such as a surgeon, to set up and execute an automated move of a tool of one of the robotic arms (which includes a tool that is coupled to the robotic arm, as well as a tool that is integrated with the robotic arm) along a single axis, such as the longitudinal axis of the tool. Such a move may be particularly advantageous when implemented as an automated biopsy of tissue, such as brain or breast tissue. The automated move may be programmed to occur during a stereotactic procedure, when some or all of the robotic arm is positioned within the bore of an open or closed magnet of a magnetic resonance imaging machine, or during a microsurgical procedure during which one or both robotic arms may be set up to and execute such an automated move. Robots that may be manipulated according to the present techniques may be characterized as computer-assisted devices.

In some embodiments, the present systems take the form of a computer system useful in simulating, planning and/or executing an automated surgical procedure. The computer system is configured to perform at least the following functions: receive data designating a target location for a tool held by a medical robot; receive data designating a second location for the tool from which the tool will move toward the target location during an automated movement; and move the medical robot in response to a user command to begin the automated movement such that the tool moves along a single axis defined by the second location and the target location. The data designating the target location may comprise coordinates (e.g., Cartesian coordinates) of the tip of the tool, or coordinates of a location spaced away from the tool along a longitudinal axis of the tool, in any suitable coordinate system, or data sufficient to enable determination of such coordinates (such as joint values of the robotic arm that allow forward kinematics to be used to solve for the coordinates based on known parameters such as robotic arm link lengths).

In some embodiments, the present devices take the form of a computer readable medium comprising machine readable instructions for receiving a command to restrict movement of an instrument held by or integral with a robotic arm along a single axis, the robotic arm being configured for use in surgery; receiving a position and orientation of an input device, the input device being linked to the robotic arm through a master-slave relationship in which the input device is the master, the difference between the position and orientation of the input device and a previous position and orientation of the input device corresponding to a desired movement of the instrument; and sending a signal or signals to effect a move of the instrument in accordance with the desired movement, where the move will be along the single axis and will not include any movement along any different axis from the single axis. The signal or signals may be any suitable form of data that includes information sufficient to cause the robotic arm to move appropriately. For example, the signal or signals could represent a set of joint displacements and/or joint velocities outputted to a local controller for the robotic arm or directly to the individual joint actuators.

In some embodiments, the user may set up a procedure by delivering inputs to a computer system through an input device, such as a hand controller that is linked as a master to the robotic arm in a master-slave relationship. The user may also deliver inputs through one or more graphical user interfaces (GUIs) using any suitable input device, such as touch screen controls (e.g., buttons, slider bars, drop down menus, tabs, etc.), a mouse, or the like. Some embodiments of the present systems are computer systems that may be configured to display on a display screen a GUI that allows the user to select a simulation mode (e.g., through a control such as a button that can be selected via a touch, a mouse, or the like) for setting up the automated movement and otherwise for training. The computer system also may be configured to display on the GUI one or more controls (e.g., that can be selected via a touch, a mouse, or the like) for selecting the type of surgery, such as microsurgery, stereotaxy with one of the robotic arms, or stereotaxy with the other robotic arm. The computer system also may be configured to display on the GUI one or more controls (e.g., that can be selected via a touch, a mouse, or the like) for activating power to: the robotic arms (e.g., through separate buttons); a base motor for adjusting the height of the base on which the robotic arms sit during microsurgical procedures; a digitizing arm usable during the physical registration process for registering a structure (e.g., of a radio-frequency coil assembly) associate in a fixed relationship with a portion of a subject to one or both robotic arms; a field camera usable during microsurgery to capture images of the surgical field; and a bore camera or cameras to be positioned in the bore of a magnet of a magnetic resonance imaging machine. The computer system also may be configured to display on the GUI one or more controls (e.g., that can be selected via a touch, a mouse, or the like) for activating a single axis lock (e.g., a Z-axis lock) and another button or buttons for controlling which robotic arm to associate the single axis lock with.

The computer system also may be configured to display on one or more additional display screens one or more additional GUIs for displaying two-dimensional images (one at a time) of a portion of a subject and for displaying a three-dimensional representation (e.g., a set of 2D images that form a 3D dataset of images representing a volume) of a portion of a subject. When only one such GUI is provided on one additional display screen, the computer system may be configured to display one or more controls (e.g., buttons, tabs, or the like that can be selected via a touch, a mouse, or the like) that a user can select to display either 2D images (one at a time) or a 3D image. The computer system also may be configured to display a zoom button, slider bar, or the like (e.g., that can be selected/manipulated via a touch, a mouse, or the like) that will allow a user that has selected the 2D display to zoom in on a given 2D image, where the 2D image remains centered as it is enlarged or reduced in size. The computer system also may be configured to display controls (e.g., that can be selected via a touch, a mouse, or the like) that allow a user to turn on a tracking feature for one of the two robotic arms that will be displayed as crosshairs representative of the location of either (a) the working tip (e.g., the distal tip) of a tool of the robotic arm selected or (b) the end of a line that extends from the tool tip, and further may be configured to display controls (e.g., buttons, slider bars, or the like that can be selected via a touch, a mouse, or the like) that allow a user to activate the display of the extension line and control the length of the extension line. As a user manipulates an input device linked to a selected robotic arm, and the user's movement alters (in simulation mode, in which the robotic arm does not actually move) the position of the tool held by/integrated with the robotic arm, the crosshairs move as a result, and the displayed 2D image (if in 2D display mode) changes to match the would-be depth of the tool (or extension line) relative to the subject. Alternatively, a given 2D image may comprise an oblique slice that is oriented perpendicular to the tool axis. Such slices interpolate pixels between the 2D slices to achieve off-axis images. Likewise, the 3D image also changes in response by 2D slices that make up the 3D image being taken away or added depending on the depth of the tool/extension line into the subject.

The computer system may also be configured to display, when either the 2D or 3D display is selected, a section corresponding to planning for an automated biopsy that includes a display of controls (e.g., that can be selected via a touch, a mouse, or the like) that can be used to set a target location (associated with a location of the crosshairs at the time when the target location button is selected) for an automated movement along a single axis (e.g., an automated biopsy); a second point (characterizable as a start point, though a given movement may not begin exactly at the start point; the second point being associated with a location of the crosshairs at the time when the second button is selected) that together with the target location defines a path for the tool movement; a tool alignment function, that can be used when a user desires to position the relevant robotic arm in place (e.g., within a preset distance, ranging from zero to some relatively small distance (e.g., 2 centimeters)) for the automated move procedure, and that when pressed will move the robotic arm so that the tool tip is positioned on or near the start point; and an execute function that a user can press in order to start the automated move of the tool, provided that the user enables the input device (e.g., by holding the input device and pushing a button on the input device with the user's finger). The computer system may also be configured to display an indicator (e.g., a colored circle) for the target location selected by the user; a line extending from the indicator and to the tool tip or extension line tip (whichever is used) following selection of the target location, the line being designed to show the user the path through the subject if the line is followed, the computer system being configured to alter the appearance of the line when a second point is selected (e.g., changing the line's color or shape).

Thus, in some embodiments, the computer system may be configured to perform at least the following functions: receive a command (e.g., through a user's touch of the screen displaying the relevant GUI) identifying a target location for a tool used in an automated movement by a robotic arm; receive a command identifying a starting location for the tool; receive a command to execute an automated move along a path (e.g., a line) defined at least in part by the starting location and the target location; and execute the automated move such that the tool, which may have a longitudinal axis, travels along the path (e.g., along a single axis). That path also may be aligned with the tools longitudinal axis. In some embodiments, the computer system may also be configured to receive (e.g., prior to the command identifying the target location) a command selecting which robotic arm to use for the automated move. In some embodiments, the computer system may also be configured to receive (e.g., prior to the command identifying the target location) a command indicating a simulation and/or setup mode that disengages an input device that is linked in a master-slave relationship to a robotic arm holding or integrated with the tool, such that in the simulation mode movement of the input device does not cause movement of the robotic arm. In some embodiments, the computer system may also be configured to receive a command (e.g., prior to the command identifying the target location) indicating a user's activation of the input device (such as through the user touching a button on in the input device with the user's hand), which activation allows the user to alter the position of the tracking indicator showing the location of the would-be tool tip relative to the image(s) of the subject as the user determines where to position the tracking indicator for selection of the target and starting locations. In some embodiments, the computer system may also be configured to receive a command (e.g., after the command identifying the starting location) indicating a new (e.g., a second) target location. In some embodiments, the computer system may also be configured to receive a command (e.g., after the command identifying the starting location) indicating a new (e.g., a second) starting location. In some embodiments, the computer system may also be configured to receive a command (e.g., after the command identifying the starting location) indicating termination of the simulation and/or setup mode. In some embodiments, the computer system may be configured to display on a GUI a control (e.g., that can be selected via a touch, a mouse, or the like) that can be used to select a mode in which the input device is engaged with the robotic arm in a master-slave relationship. In some embodiments, the computer system may be configured to receive a command, when in the master-slave mode, enabling the input device (e.g., by holding the input device and pushing a button on the input device with a finger of the user). In some embodiments, the computer system may be configured to receive a command to execute the automated move along a path that is defined at least in part by the starting and target locations, the computer system also be configured to cause the robotic arm in a way that moves the tool in a single axis along the path only after it has received a command indicating the input device is enabled (e.g., such that a user must be holding the input device in order for the automated move to proceed). The computer system may be configured to stop the robotic arm from completing the automated move if it receives a command to stop the automated move (e.g., through a user pushing the same button on the input device that otherwise enables the input device), and may also be configured to display on a GUI a message that includes buttons or the like (e.g., that can be selected via a touch, a mouse, or the like) for continuing with the automated move, reversing direction, or stopping, and may be configured to receive a command to either continue, reverse direction or stop, depending on the button or the like that is activated, provided it first receives a command indicating the input device is enabled (e.g., by holding the input device and pushing a button on the input device with the user's finger).

Any embodiment of any of the present methods, devices, and systems may consist of or consist essentially of—rather than comprise/include/contain/have—the described steps and/or features. Thus, in any of the claims, the term "consisting of" or "consisting essentially of" may be substituted for any of the open-ended linking verbs recited above, in order to change the scope of a given claim from what it would otherwise be using the open-ended linking verb.

BRIEF DESCRIPTION OF THE FIGURES

The following drawings illustrate by way of example and not limitation. Identical reference numerals do not necessarily indicate an identical structure, system, or display. Rather, the same reference numeral may be used to indicate a similar feature or a feature with similar functionality. Every feature of each embodiment is not always labeled in every figure in which that embodiment appears, in order to keep the figures clear. The hand controllers, manipulators and tools shown in the figures are drawn to scale, meaning the sizes of the depicted elements are accurate relative to each other.

FIG. 1A is a perspective view of one embodiment of two input devices (hand controllers) that may be used consistent with the present techniques.

FIGS. 1C-1E are different views showing a tool held by a robotic arm located in a first position of a stereotactic procedure.

FIGS. 2A-2C are different views showing the tool from FIGS. 1C-1E in a second position of a stereotactic procedure.

DETAILED DESCRIPTION OF ILLUSTRATIVE EMBODIMENTS

The terms "comprise" (and any form of comprise, such as "comprises" and "comprising"), "have" (and any form of have, such as "has" and "having"), "contain" (and any form of contain, such as "contains" and "containing"), and "include" (and any form of include, such as "includes" and "including") are open-ended linking verbs. As a result, a method, device, or system that "comprises," "has," "contains," or "includes" one or more recited steps or elements possesses those recited steps or elements, but is not limited to possessing only those steps or elements; it may possess (i.e., cover) elements or steps that are not recited. Likewise, an element of a method, device, or system that "comprises," "has," "contains," or "includes" one or more recited features possesses those features, but is not limited to possessing only those features; it may possess features that are not recited. Similarly, a computer readable medium "comprising" (or "encoded with") machine readable instructions for performing certain steps is a computer readable medium that has machine readable instructions for implementing at least the recited steps, but also covers media having machine readable instructions for implementing additional, unrecited steps. Further, a computer system that is configured to perform at least certain functions is not limited to performing only the recited functions, and may be configured in a way or ways that are not specified provided the system is configured to perform the recited functions.

The terms "a" and "an" are defined as one or more than one unless this disclosure explicitly requires otherwise. The term "another" is defined as at least a second or more. The terms "substantially" is defined as at least close to (and includes) a given value or state (preferably within 10% of, more preferably within 1% of, and most preferably within 0.1% of).

In some embodiments, the invention is a software enabled single-axis lock for movement of a tool along the single axis by a robotic arm with multiple degrees of freedom. The software solution allows a robotic arm with an unlimited number of degrees of freedom to behave in the same fashion as a robot or device that is mechanically restricted to motion of its tool along the single axis. Prior to a procedure, a command may be sent to the software to lock the motion by a given robotic arm of its tool (meaning a tool the robotic arm is holding or that is integral with the robotic arm; the present tools may be characterized more specifically as medical tools or surgical tools) in a single axis using any suitable input device, such as a button on a touch screen on a GUI, a button on an input device (e.g., a hand controller), or the like.

Figure 1B:
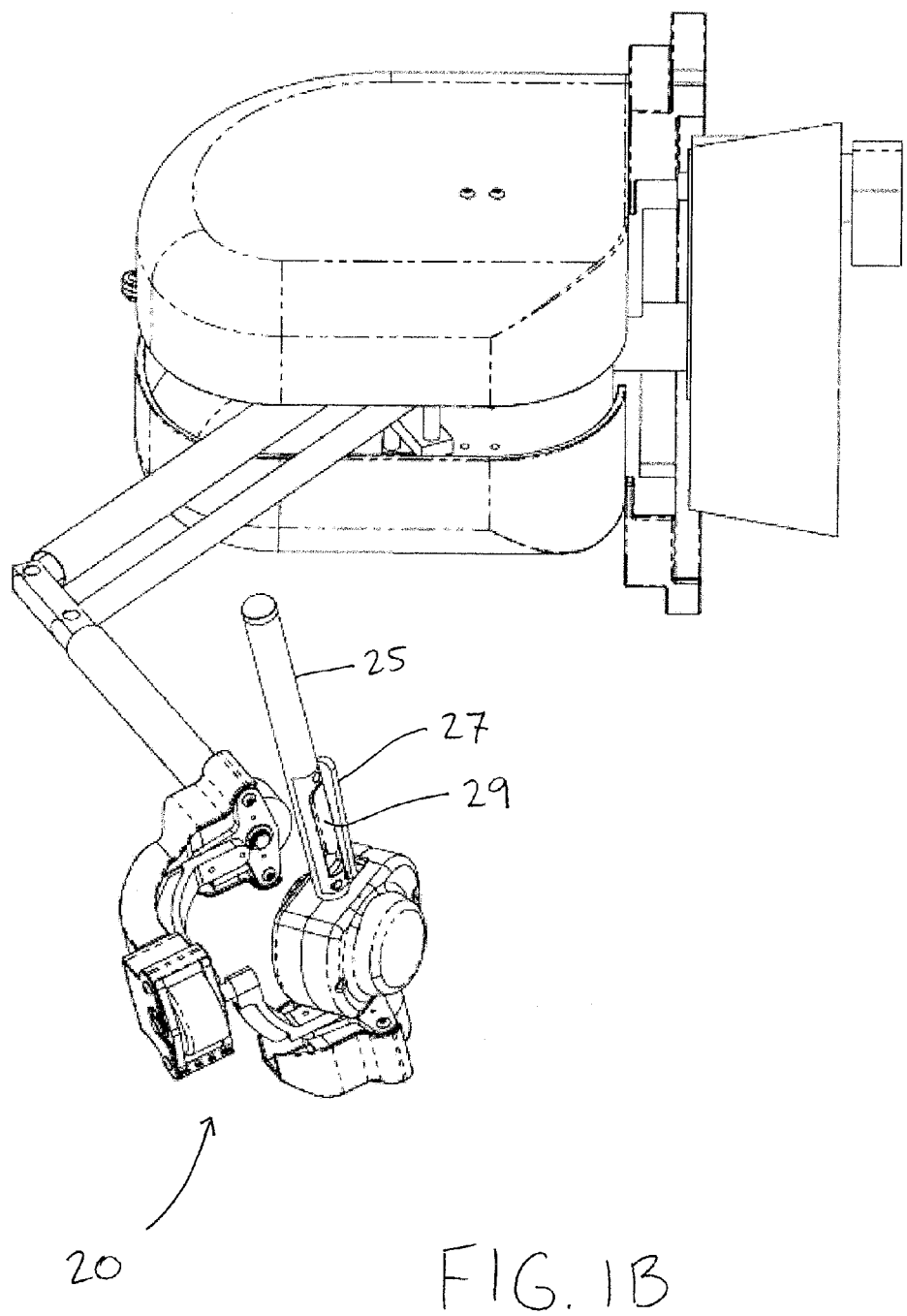
FIG. 1B is an enlarged view of a left-handed input device.

The apparatus to which the inventive techniques may be applied may, in some embodiments, include a slave robotic arm commanded by a master input device, such as a hand controller. An example of a pair of input devices (in the form of hand controllers) that can be used to control two different robotic arms, respectively, of a medical or surgical robotic system are shown in FIG. 1A. Input devices 20, which are mirror images of each other, each includes a stylus 25 that can be held like a long pen, lever 27 that can be squeezed toward stylus 25 to cause a tool integrated with or held by the slave robotic arm to actuate (e.g., squeezing lever 27 can cause forceps to close), and an enable/disable button 29 that can be touched and held for a short amount of time in order to activate the input device. One way to hold input devices 20 is to grasp stylus 25 so that lever 27 can be squeezed with the forefinger and so that button 29 can be touched with the thumb. FIG. 1B shows an enlarged view of the left-handed input device 20.

Closed or open form forward and inverse kinematic solutions may be created such that an individual with ordinary skill in the art can use the joint values characterizing the position of each joint of the robotic arm to solve for a commanded tool tip position (taking into consideration the permitted axis of movement), and then take that commanded tool tip position and solve for the joint angles that must be achieved to move the surgical tool to the commanded tool tip position along a single axis.

One manner of creating a non-mechanical single-axis tool movement lock (after, for example, a command has been received to create one) involves the following:

a) retrieving an input device (e.g., hand controller) command in tool tip space (e.g., Cartesian X, Y, Z, roll, pitch, yaw). This retrieving may comprise receiving a hand controller signal(s) (command(s), or data) signifying the position and orientation of the hand controller; determining (e.g., calculating) a delta value of the movement of the hand controller in a single axis (e.g., an axis that is related by a transformation to the single axis to which tool tip movement is restricted); and determining a corresponding delta value for the tool tip using that hand controller delta. If a transformation from delta values in hand controller space to delta values in tool tip space is determined, all tool tip delta values may be ignored except the delta along the relevant single axis. This could effectively be achieved by either a simple zeroing of non single axis parameters received from the hand controller or calculating all the delta values for each axis and using only the delta value in the single axis direction.

b) take the current position of the manipulator (which is a term that can describe the robotic arm) and perform a forward kinematic solution to get tool tip X, Y, Z, roll, pitch, yaw.

c) add the single axis delta determined in step a) to the current manipulator tip position determined in step b).

d) using this new tip position, perform an inverse kinematics to solve for the required joint angles.

e) command the manipulator to the new joint values.

f) repeat from step a).

In some embodiments, the rate of execution of the above loop may be arbitrarily small to produce linear motion at the tool tip. The longer the time or the bigger the steps taken, the more non-linearity can be created as the motion between each Cartesian position is in joint space, and joints are interpreted linearly over the desired range of travel. Smaller motions on the order of 10 milliseconds result in imperceptible non-linearities between each Cartesian tip command and an effective linear motion.

Furthermore, as discussed in more detail below, in some embodiments the movement of a tool along a single axis may be pre-programmed so as to be automated.

Referring now to FIGS. 1C-3C, detailed views of a manipulator 100 and a surgical tool 150 are shown in various positions as the manipulator 100 causes movement of the tool along a single axis in a stereotactic procedure (such a movement also may be achieved in any other procedure, such as a microsurgical procedure). Manipulator 100, which is an example of a multi-degree of freedom robotic arm (specifically, manipulator 100 may be characterized as a six degree of freedom slave manipulator, and it is similar in functionality and operation to the robotic arms disclosed in the '316 patent), assembly 200 comprising a head clamp and radiofrequency coil device (which is coupled to the head clamp, and which can be further coupled to the operating room table by a fixable multi link arm), and cameras 190 (only one of which is visible (the other is on the opposite side of the extension board)) are coupled to an extension board 260. Extension board 260 may be coupled to any suitable table or other structure having a patient support surface (not shown). In the views shown, a schematic drawing of a patient's head 300 is shown held by the head clamp of assembly 200.

Figure 1C:
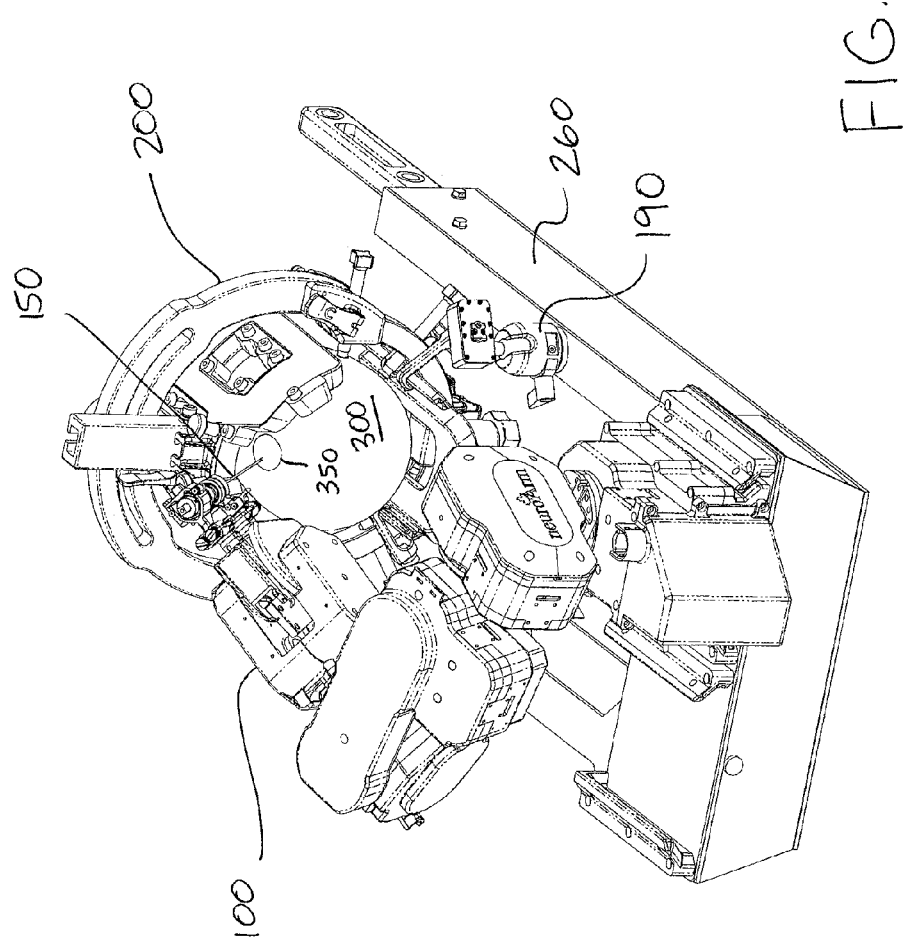
Figure 1E:
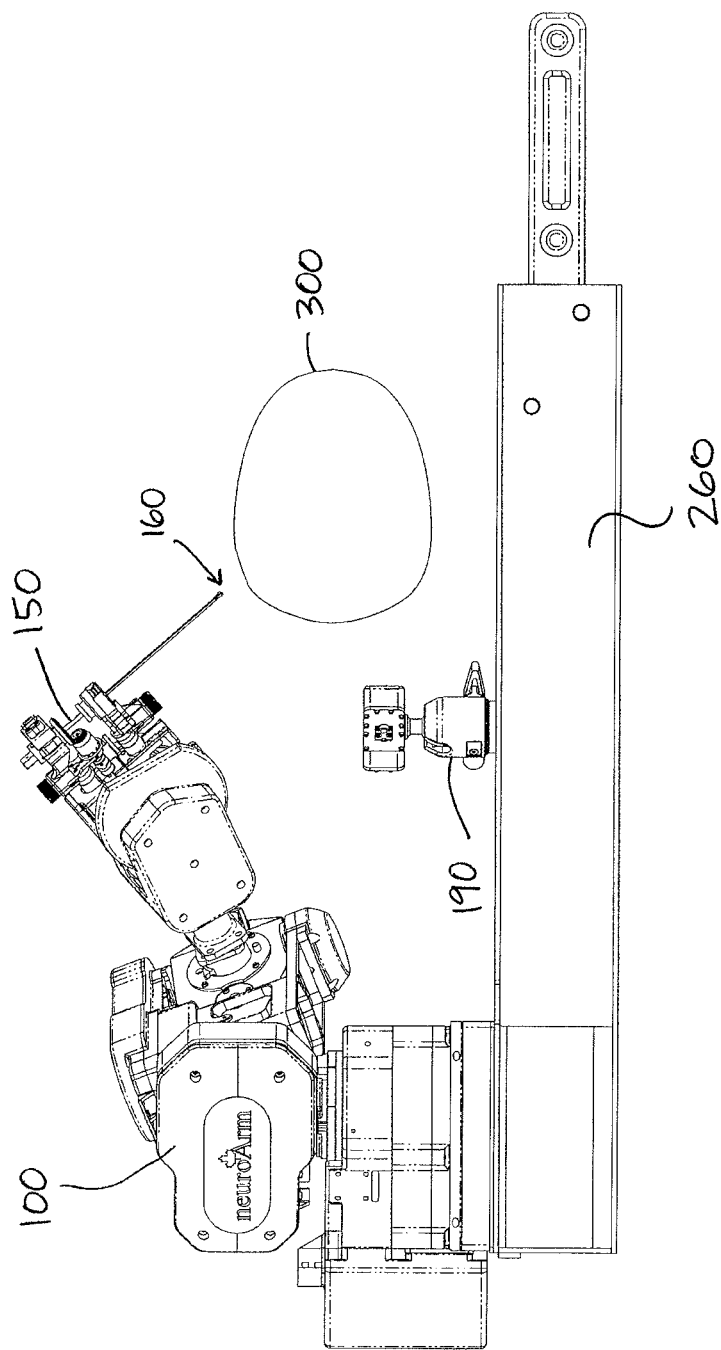
Figure 2B:
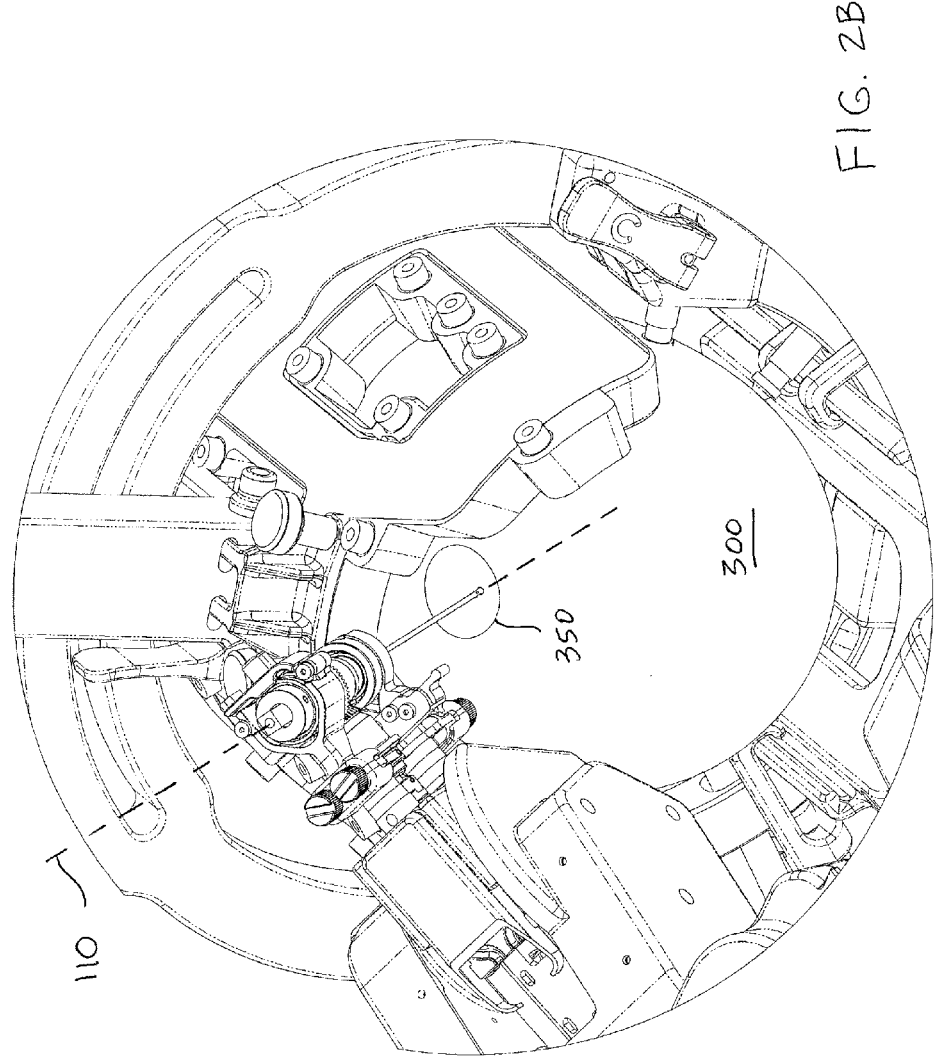
Figure 2C:
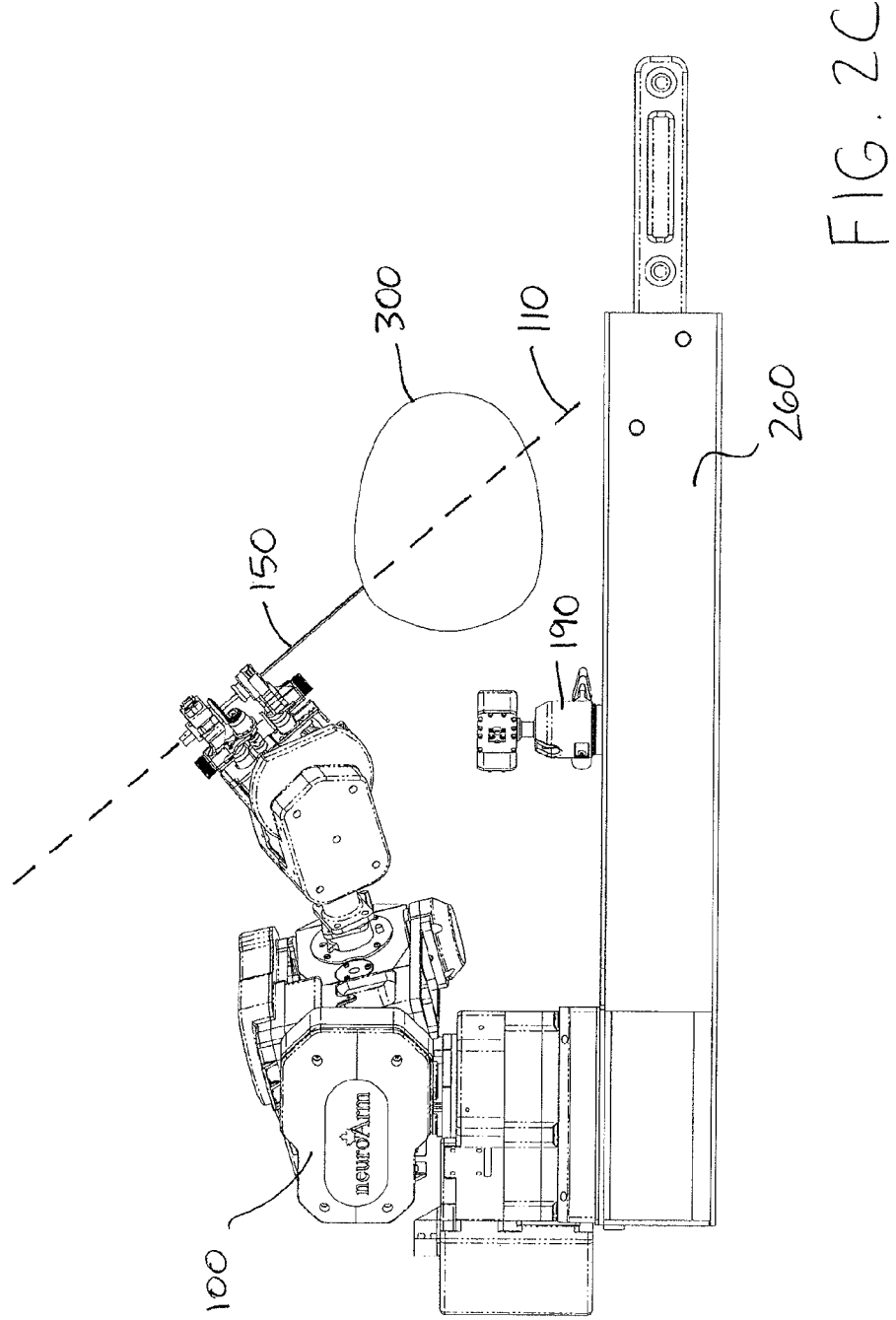
Figure 3A:
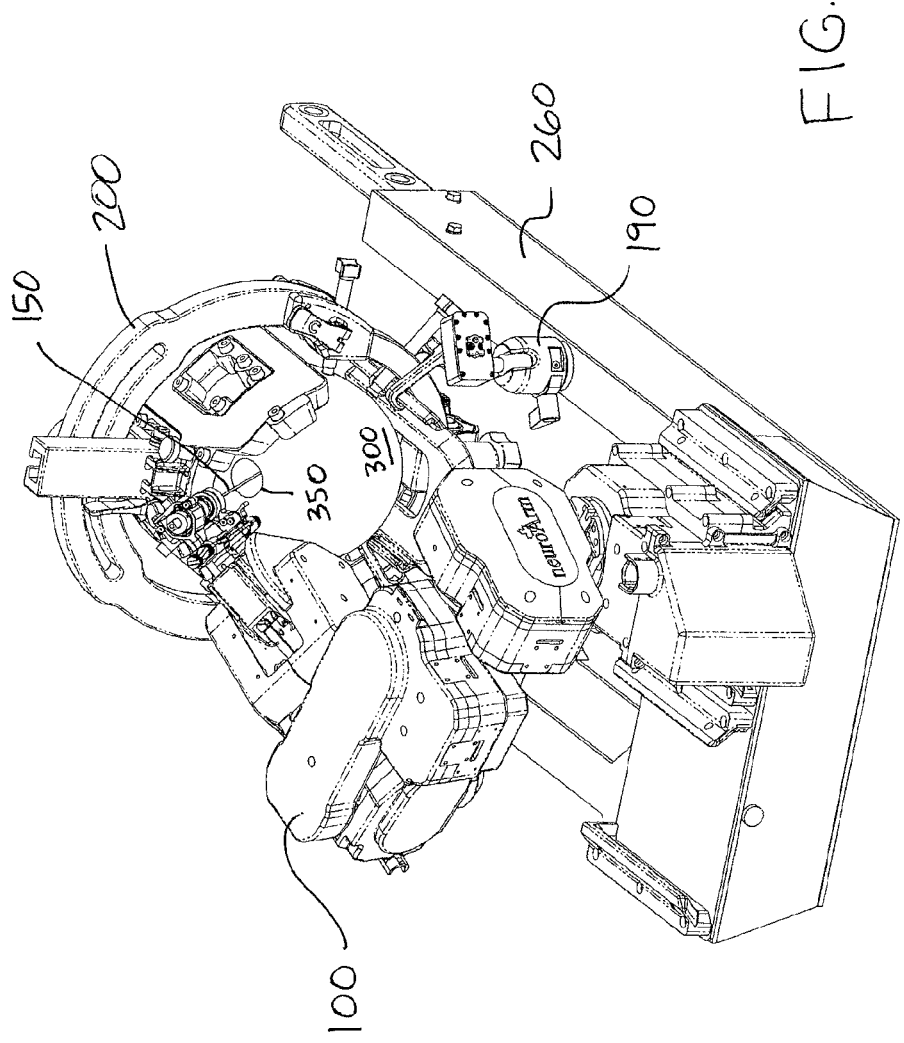
FIGS. 3A-3C are different views showing the tool from FIGS. 1C-1E in a third position of a stereotactic procedure.
Figure 3B:
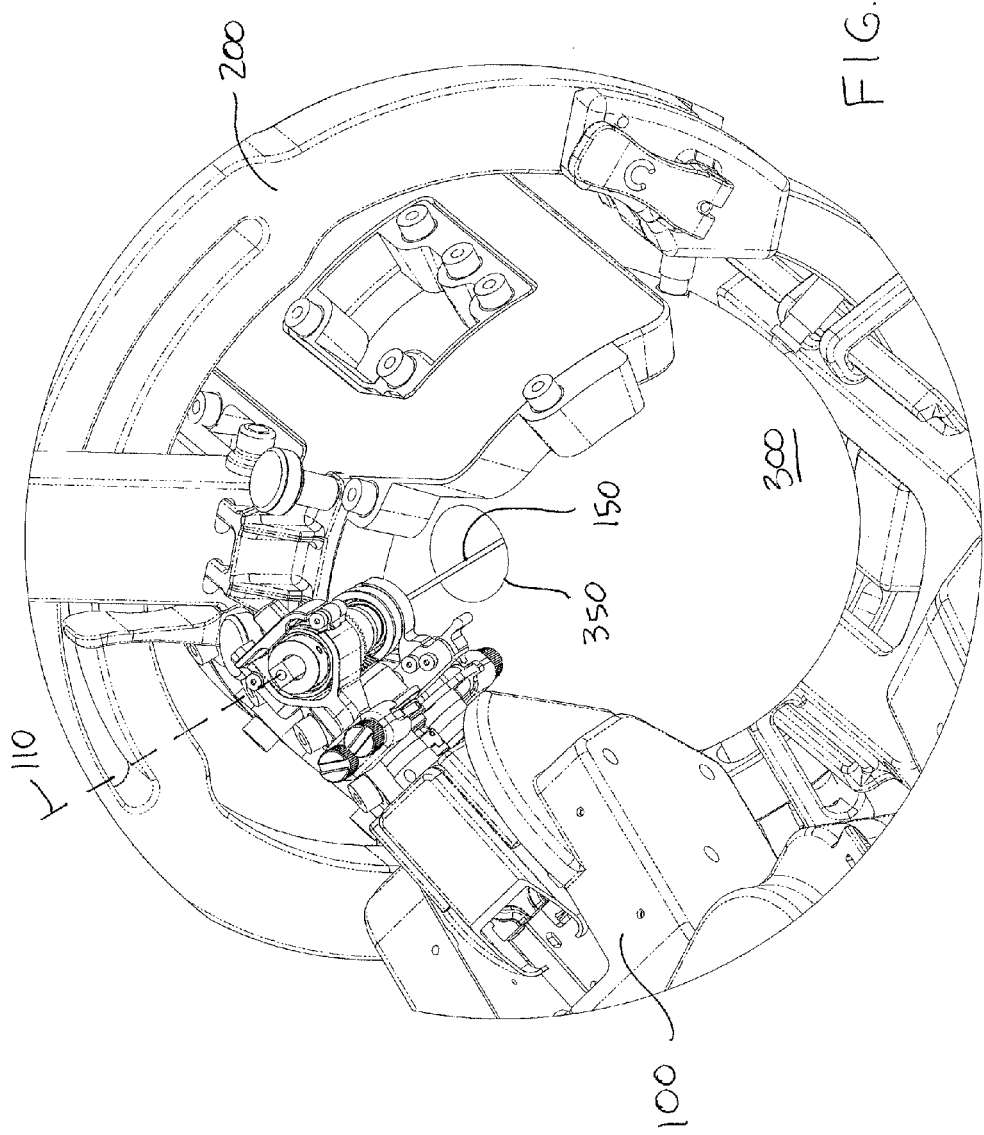
Figure 3C:
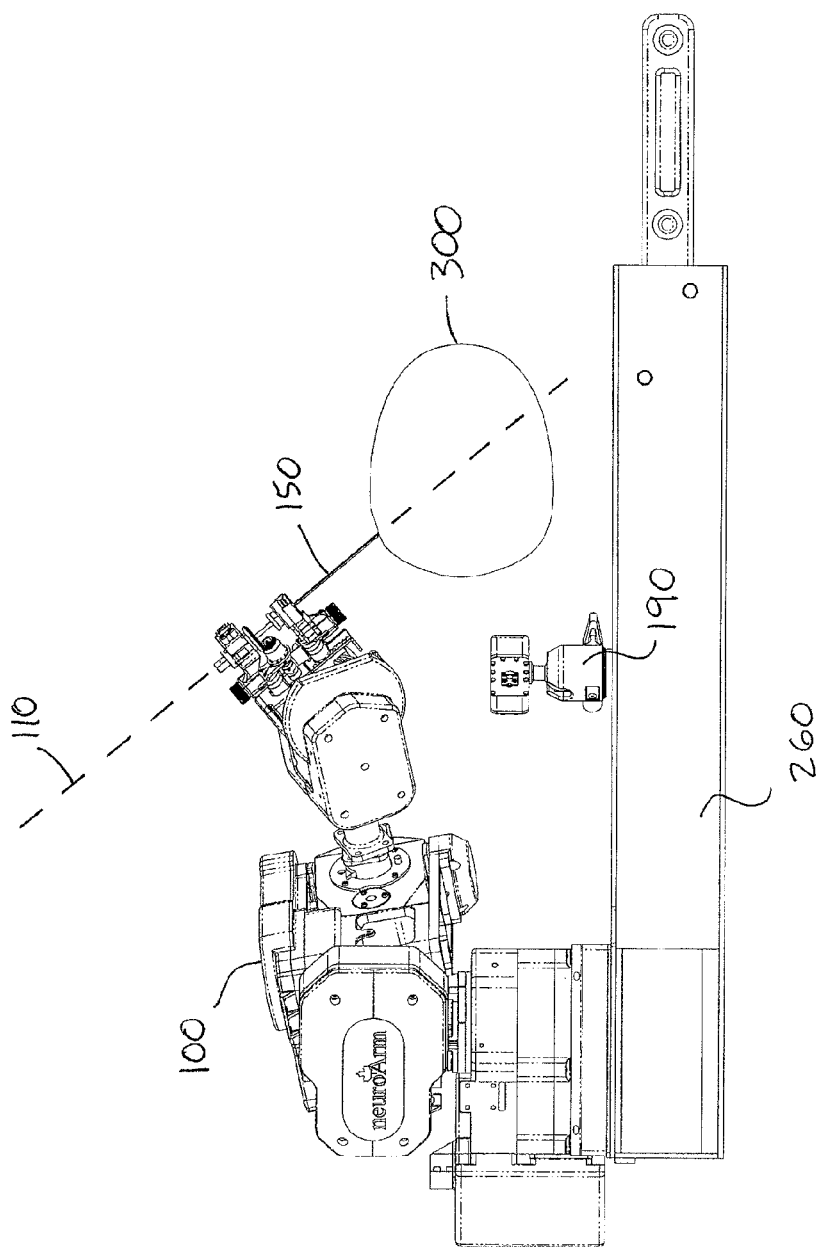

FIGS. 1C and 1D show manipulator 100 in a first position in which surgical tool 150 is located outside of head 300, near opening 350 in head 300, which may be a burr hole or any other suitable surgical opening. However, tip 160 of surgical tool 150 is outside of opening 350. FIG. 1E is a side view of the position shown in FIGS. 1C and 1D, and does not include assembly 200 for clarity. FIGS. 2A and 2B show manipulator 100 moved to a second position in which tip 160 of surgical tool 150 has been advanced along axis 110, and no other axis, by manipulator 100 so that tip 160 has penetrated the boundary of opening 350. FIG. 2C is a side view of the position shown in FIGS. 2A and 2B, and does not include assembly 200 for clarity. FIGS. 3A and 3B show manipulator 100 moved to a third position in which tip 160 has moved along axis 110 into a location within head 300, which it can be further manipulated by a user/operator (e.g., a surgeon) to perform any of a number of functions, such as taking a biopsy of tissue. FIG. 3C is a side view of the position shown in FIGS. 3A and 3B, and does not include assembly 200 for clarity. Axis 110 is substantially aligned (perfectly aligned in the depicted embodiment) with the longitudinal axis (not separately shown) of tool 150. For other tools that have bends or angles, the tool and tool tip will still move along a single axis, however that axis may not coincide with a longitudinal axis of the tool itself.

Figure 4:
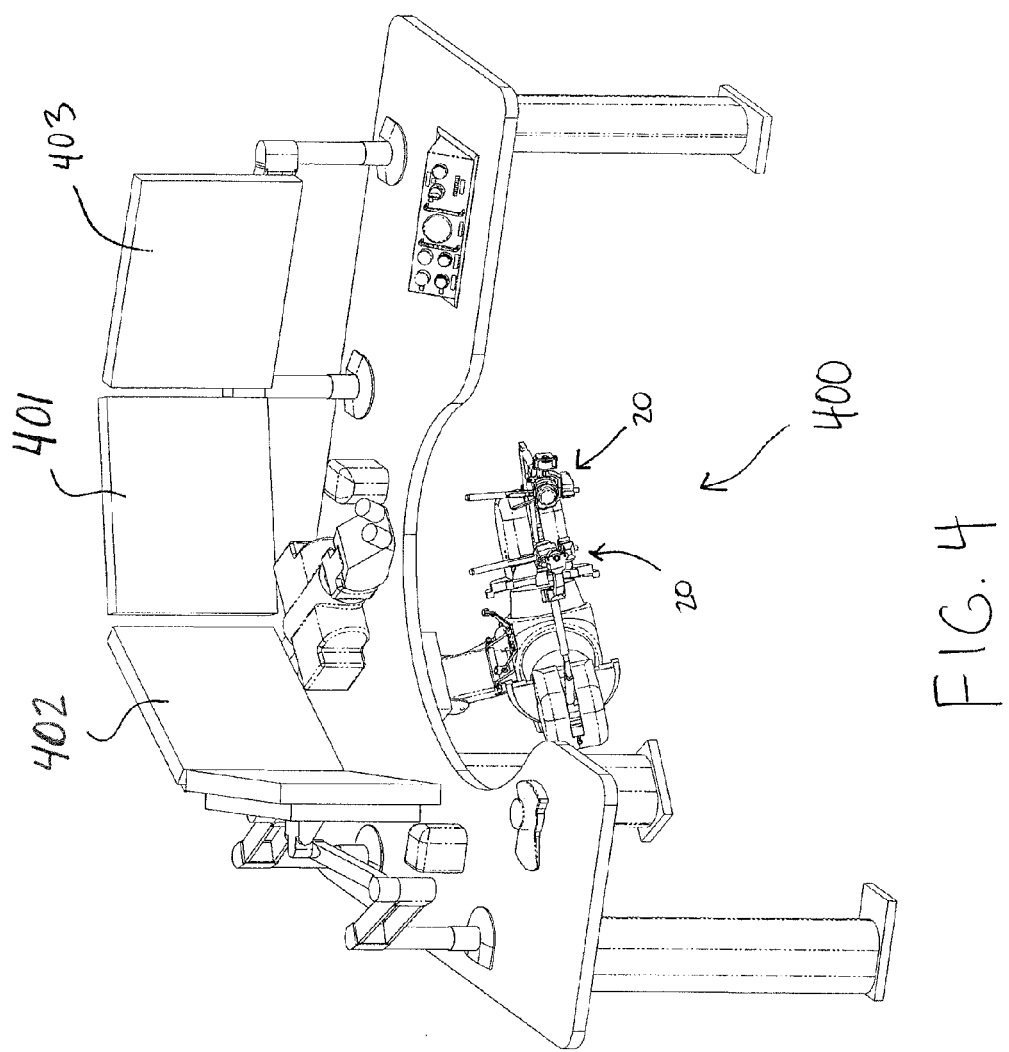
FIG. 4 is a perspective view of a workstation for use in planning and controlling the tool movement shown in FIGS. 1C-3C.

FIG. 4 illustrates a perspective view of a workstation 400 that can be used to control manipulator 100 (or two such manipulators) and surgical tool 150 (or two such surgical tools, one held by each of two such manipulators). In certain embodiments, workstation 400 comprises input devices 20 shown in FIGS. 1A and 1B to control movement of manipulator 100. Workstation 400 may include a table to which the input devices are secured as well as a series of display screens, including display screens 401 and 402, each of which can provide a graphical user interface (GUI) that can be used in setting up a procedure using manipulator 100. In a preferred embodiment, the GUI shown on display screen 401 may be used to select two points that will define the axis (or path or trajectory) along which the tip of the relevant tool travels in an automated single axis movement (such a screen is referred to as a command status display (CSD) in this document) and the GUI shown on display screen 402 may be used to display one or more images from a three-dimensional dataset of images of a subject taken using a three-dimensional imaging device, such as a magnetic resonance imaging device, which may be viewed as a determination is made by an operator about which points to select on display screen 402 (such a screen is referred to in this document as a magnetic resonance image display (MRID)). The other display screens depicted in FIG. 4 may be used to show other images or displays associated with a given procedure involving one or both manipulators 100.

FIGS. 5-11 illustrate various screen displays that can be used as GUIs for displays 401 and 402. As shown in the figures, multiple controls (such as buttons, slider bars, radio buttons, check boxes, drop down menus, and the like) are provided on each screen for receiving user input through any suitable means, such as through touching the screen, manipulating an input device such as a mouse, or the like. Only those controls relevant to the features presented in this disclosure will be discussed.

Figure 5:
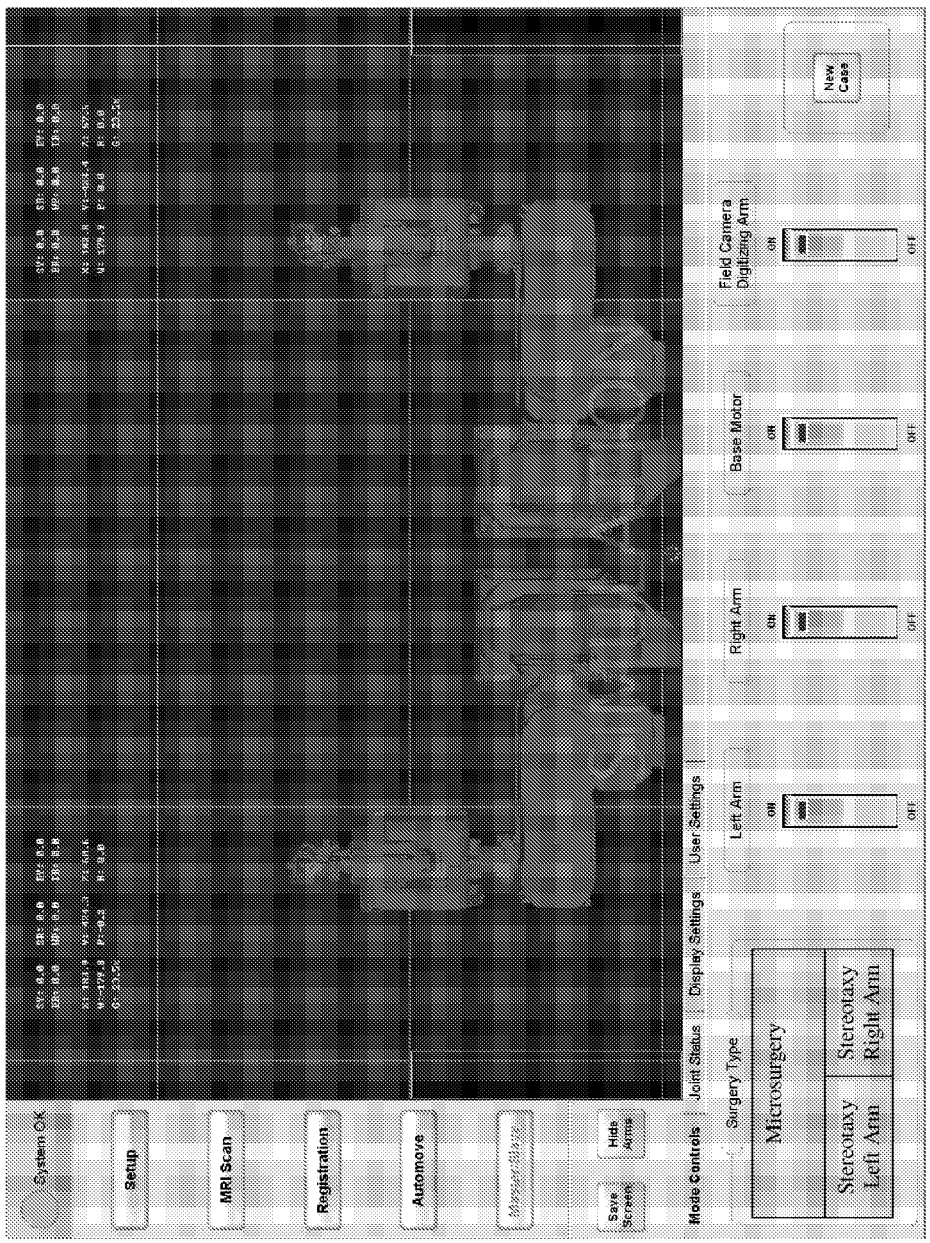
FIG. 5 shows a graphical user interface that can be used in the set up and control of the tool movement shown in FIGS. 1C-3C.

In certain embodiments, a computer system may be configured such that starting the primary application supported by the computer system brings the user to a startup screen as illustrated in FIG. 5. Those of ordinary skill in the art having the benefit of this disclosure will be able to write code (machine readable instructions, which can be implemented through software, hardware, firmware, or a combination of any two or more of these) without undue experimentation for accomplishing the features (including the graphical user interfaces) described below and shown in the figures. FIG. 5 illustrates a CSD 401 that can be used in setting up a desired mode for one or both manipulators (such as a "Z Axis Lock" representative of a manipulators ability to move its tool along only one axis) or a desired procedure, such as an automated move (e.g., along a single axis) of a surgical tool by a given manipulator 100. This display includes options for selecting procedure types (microsurgery, stereotaxy left arm, stereotaxy right arm), as well as power selections for the right arm, left arm, a base motor for adjusting the height of the arms (manipulators 100) supported on a mobile and lockable base, a field camera for capturing images during microsurgery and a digitizing arm for use in the physical part of subject image-to-manipulator registration. The power buttons are shown in the "Mode Controls" tab, as is the "Surgery Type." Manipulators 100 are shown in an unhighlighted manner on the GUI shown in FIG. 5, signifying that neither has been selected for using in either training/simulation or a procedure using the buttons at the bottom left of the screen.

A suitable technique for registering one or more two-dimensional images of a portion of a subject with one or both manipulators 100 is disclosed in co-pending International Application No. PCT/US08/60538, which is incorporated by reference. Once suitable registration has been accomplished, which may include both an MRI registration aspect to locate the imaged subject to a physical structure and a physical registration aspect to register a given manipulator to that physical structure, set up may begin.

Figure 6:
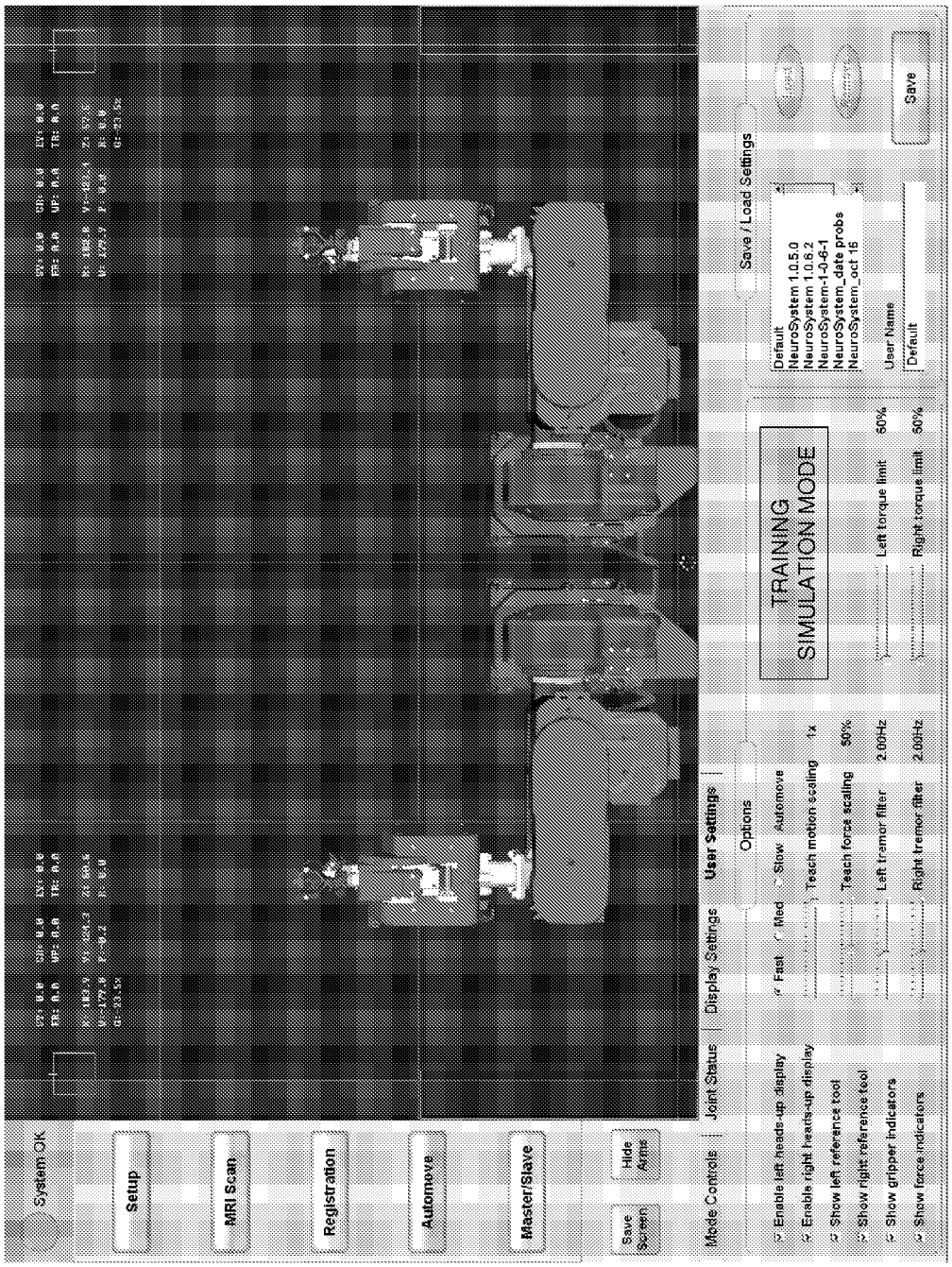
FIG. 6 shows the GUI of FIG. 5 in a training/simulation mode involving both robotic arms.

In one exemplary embodiment, a user may select a simulation mode by selecting the "Training Simulation Mode" button under the "User Settings" tab shown in CSD 401 of FIG. 6. Selecting the simulation mode can allow the user to view simulated movements of manipulator 100 and surgical tool 150 in response to movements of the input device, without causing actual movement of manipulator 100. The word "simulation" also appears near the bottom portion of the display, as shown for example in FIGS. 5-7. In simulation mode, a user can view a potential path of travel of surgical tool 150 that may be used in a surgical procedure. This allows a user to evaluate multiple potential paths of manipulator 100 and surgical tool 150 before defining one as described below for actual use in the procedure.

Figure 7:
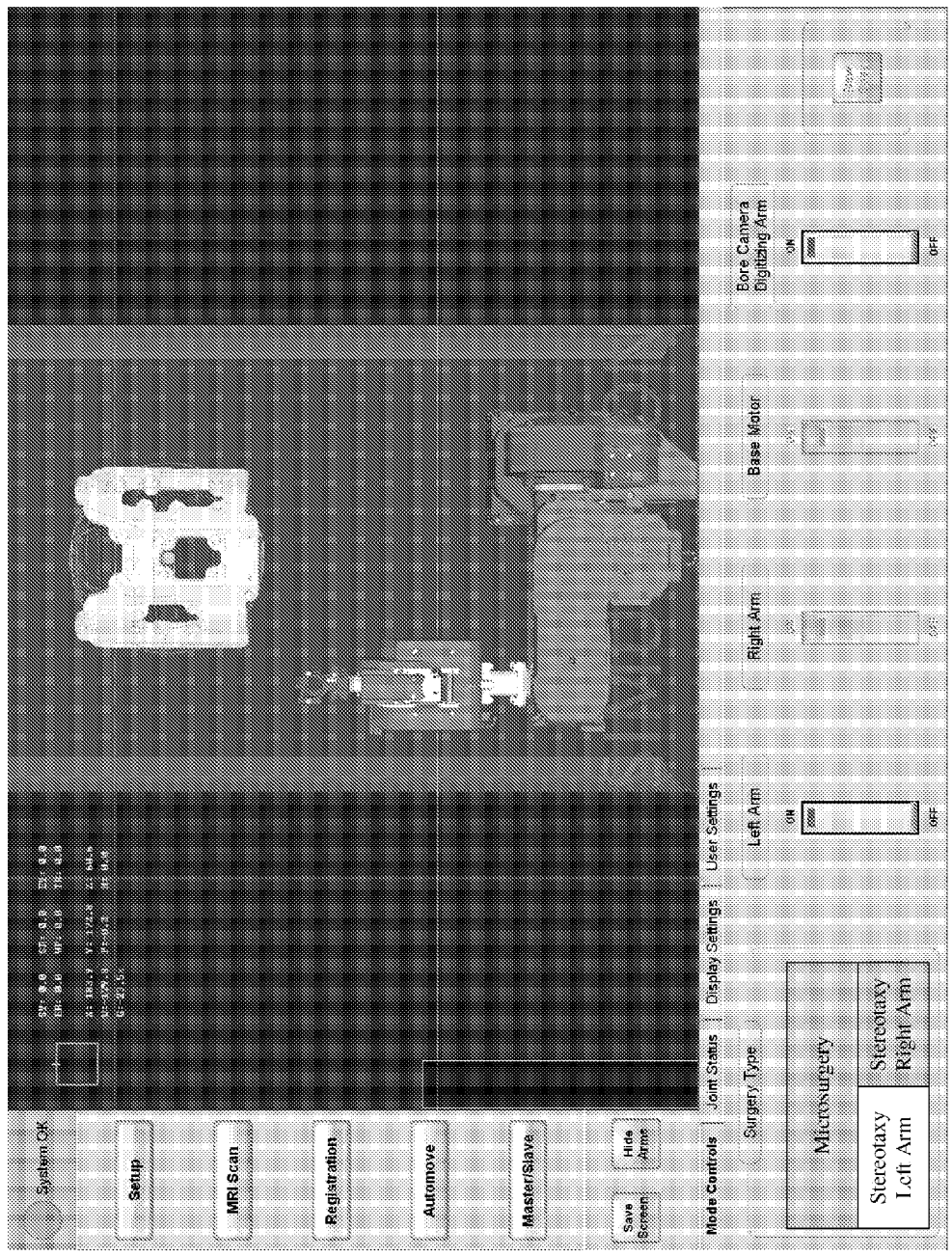
FIG. 7 shows the GUI of FIG. 5 in a training/simulation mode in which the left arm has been chosen for stereotaxy.

CSD 401 in FIG. 7 illustrates the system in simulated stereotaxy mode with the left arm enabled. This version of CSD 401 now shows only one manipulator as a result of the left arm selection, and shows it in a highlighted state. It also shows an upper portion of an RF coil device (from assembly 200) positioned over a graphical representation of a subject's head (e.g., head 300). It also shows that the user has enabled power to the left arm and a "Bore Camera" (or cameras, such as camera 190 shown in FIGS. 1C-3C, which may be exposed without being affected to the magnetic field created in an MRI environment) and the digitizing arm (note that the unselected "Right Arm" and "Base Motor" buttons are unselected and grayed out).

Figure 8:
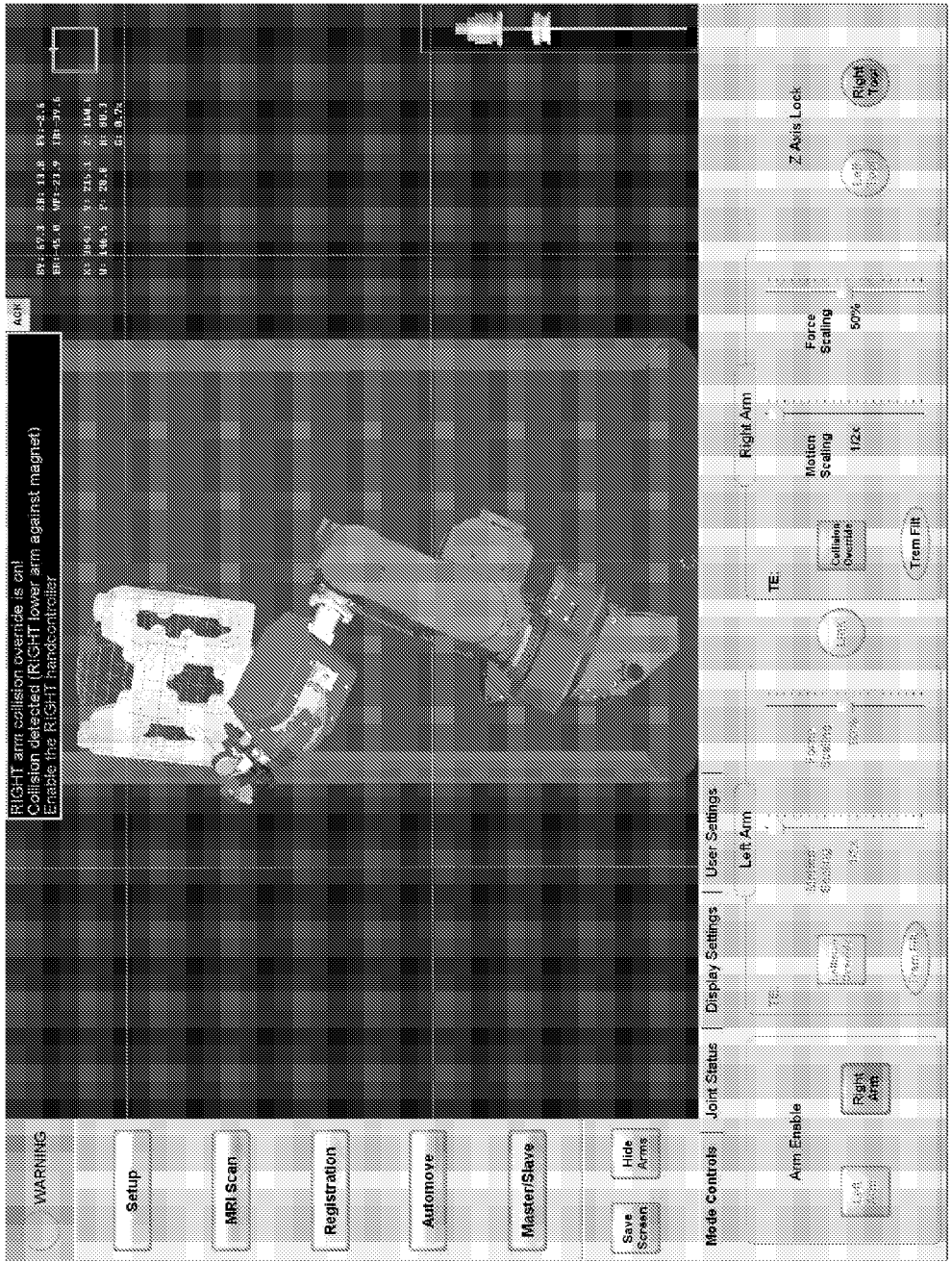
FIG. 8 shows the GUI of FIG. 5 in a training/simulation mode in which the right arm has been chosen for stereotaxy and the Z Axis Lock function for the tool of that arm has been activated.

FIG. 8 illustrates a version of CSD 401 indicating that a user has selected to place the right arm in stereotaxy mode and Z Axis Lock mode, where the tool that has been selected for use by the right manipulator is shown on the right lower part of the screen (and is the same biopsy tool shown in FIGS. 1C-3C). The mode of the displayed manipulator shown in FIG. 8 was achieved through a user's selection of stereotaxy right arm (as shown in the buttons in FIG. 5), master/slave mode via selection of the Master/Slave button shown in FIG. 8, and the enablement of the right arm by selecting "Right Arm" in the "Arm Enable" box of the "Mode Controls" tab shown in FIG. 8. Next, the user enables the input device associated with the right manipulator by depressing button 29 on right hand controller 20. Once the input device is enabled, and because the user has not put the system into training/simulation mode, the user can manipulate the enabled input device to put the manipulator into the position and orientation desired by the user for movement of the tool along a single axis. Once the manipulator is in position, the user can disable control of the manipulator by again pushing button 29; otherwise, the user can proceed to enabling the z-axis lock for the tool held by that manipulator by (in the depicted embodiment) selecting "Right Tool" in the "Z Axis Lock" box of the "Mode Controls" tab shown in FIG. 8. In this mode, the tool held by the manipulator will only travel along the axis defined (in the depicted embodiment) by the upper portion of the tool where it is held by the tool holder portions coupled to the end effector of the manipulator (which, in this embodiment, is a longitudinal axis that is centered in the entire length of tool), such travel occurring in the forward or backward directions depending on the user's motion of the input device. When the user no longer desires to lock the motion of the tool to such axis, the user can push the same "Right Tool" button to disable that mode.

Figure 9:
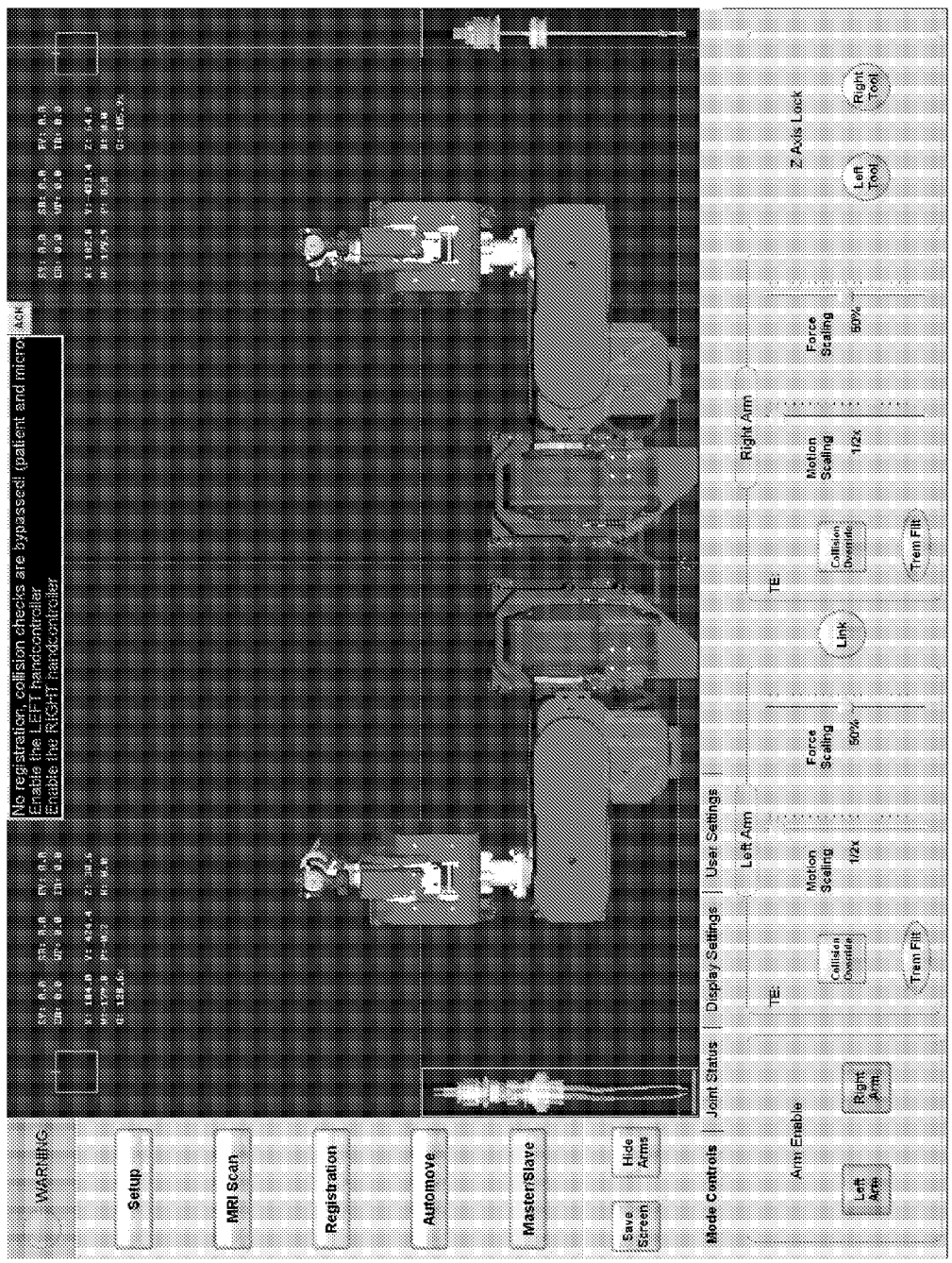
FIG. 9 shows the GUI of FIG. 5 in a training/simulation mode in which the microsurgery application has been chosen, both arms are enabled, and both tools have been chosen.

FIG. 9 illustrates a version of CSD 401 indicating that a user has selected microsurgical mode and simulation mode, and enabled both manipulators (which are both highlighted) and selected tools for them. A user may enable the Z Axis Lock function for the tools of both arms from this version of CSD 401. The selected tool for each manipulator is shown to the side of the manipulator (bipolar forceps on the left and biopsy tool on the right).

Figure 10:
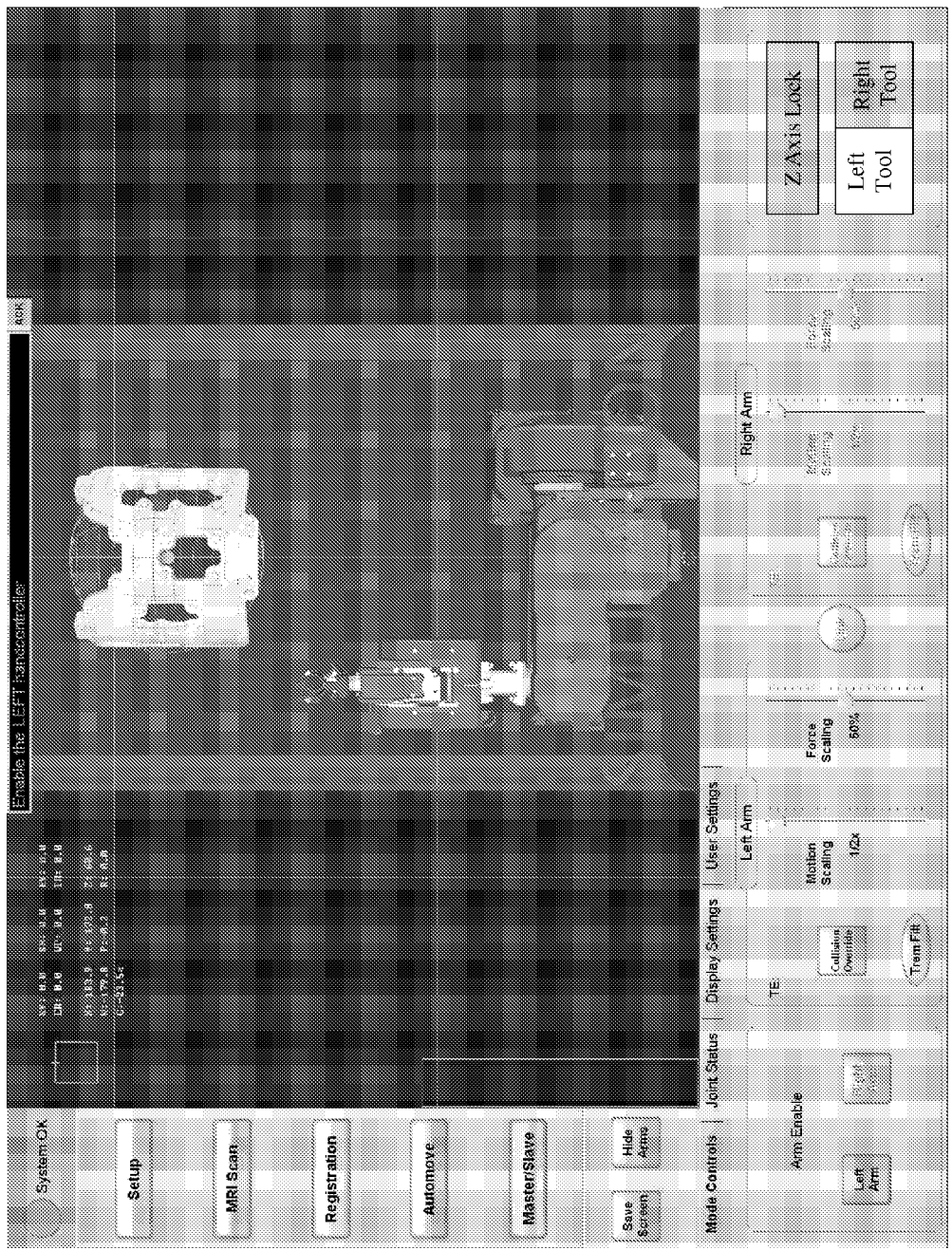
FIG. 10 shows the GUI of FIG. 5 in a training/simulation mode in which the left arm has been chosen for stereotaxy (as in FIG. 7) and the Z Axis Lock function for the tool of that arm has been activated.

FIG. 10 illustrates a version of CSD 401 in which a simulated stereotaxy left arm mode has been selected (by, for example, selecting the "Stereotaxy Left Arm" button shown in FIG. 5), the left arm has been enabled, the Z Axis Lock function has been selected for the left tool.

Figure 11:
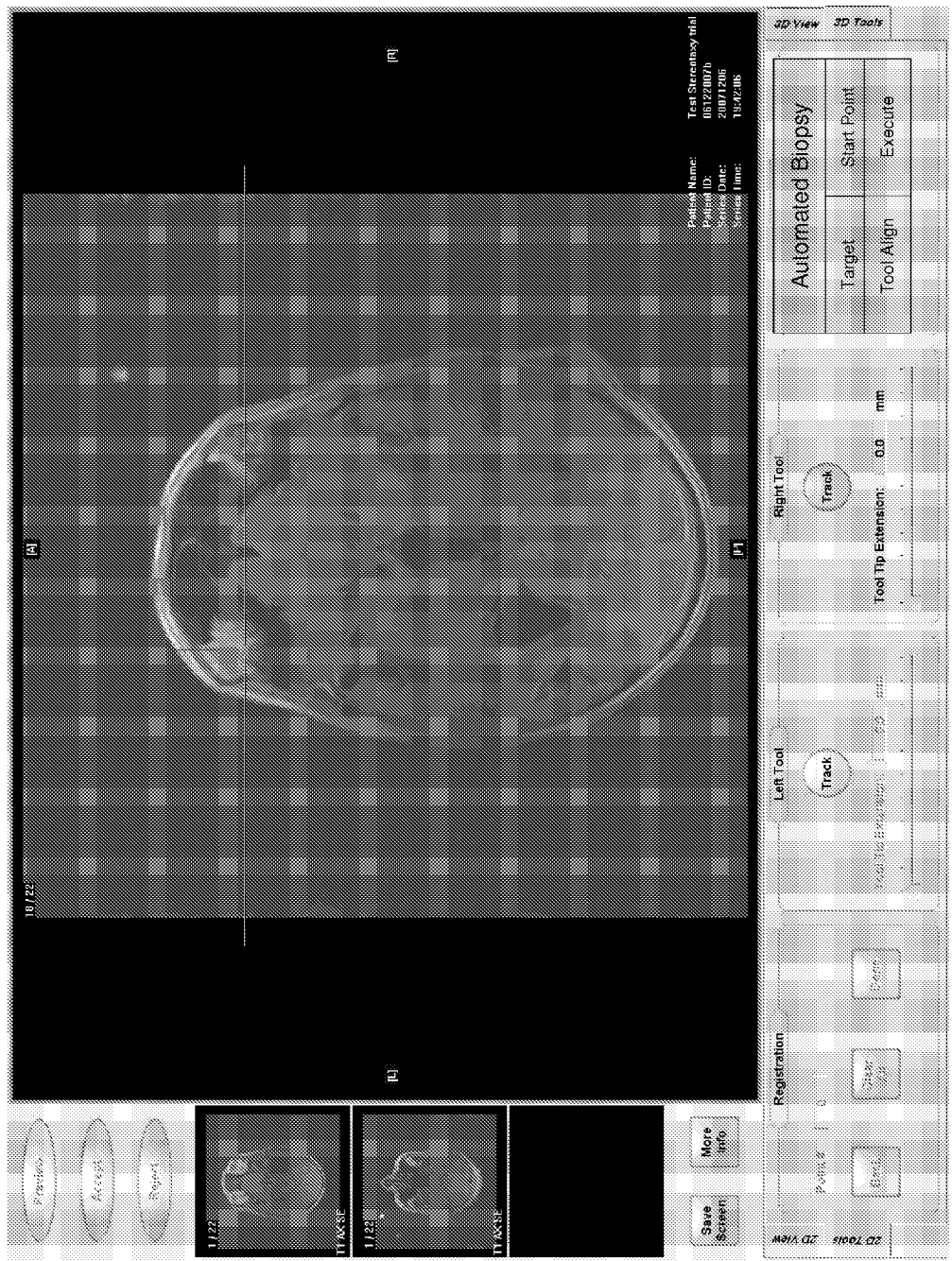
FIG. 11 shows another GUI that can be used in the set up of the tool movement shown in FIGS. 1C-3C. An indicator in the form of crosshairs corresponding to the location of the tool tip is shown on a 2D image, representing the tool tip's location relative to the portion of the subject in the 2D image.

Referring now to FIG. 11, MRID 402 depicts a GUI that allows a user to toggle between 2D and 3D views taken with a 3-D imaging modality (such as an MRI machine) of a portion (such as the head) of a subject, as reflected in the 2D tabs "2D Tools" and "2D View" at the bottom left of the screen and in the 3D tabs "3D Tools" and "3D View" at the bottom right of the screen. In FIG. 11, an indicator (in this example, crosshairs) is displayed of the location of the tip (e.g., tip 160) of the relevant tool (e.g., surgical tool 150, or, in other embodiments, the terminal end of an extension line that extends from the tool tip a distance selected using the slider bar shown underneath the "Tool Tip Extension:" box beneath the tool that is being tracked) within the portion of the subject displayed in the image or dataset of images (which can be a 3D image made of multiple slices of 2D images). In the FIG. 11 version of MRID 402, the 2D Tools tab has been selected, and a two-dimensional image is shown overlaid by the crosshairs indicator showing the location of the tip of the right tool within the subject. These crosshairs appear in response to a user selecting the "Track" button beneath the section for the relevant tool(s). By selecting the Track option on MRID 402, a user can view the MRID as he or she manipulates the relevant input device to follow (or track) the location of the tool tip (or tool tip extension line end point, and regardless of whether the user is in simulation/training mode) relative to the subject. as it travels through the subject.

Figure 12:
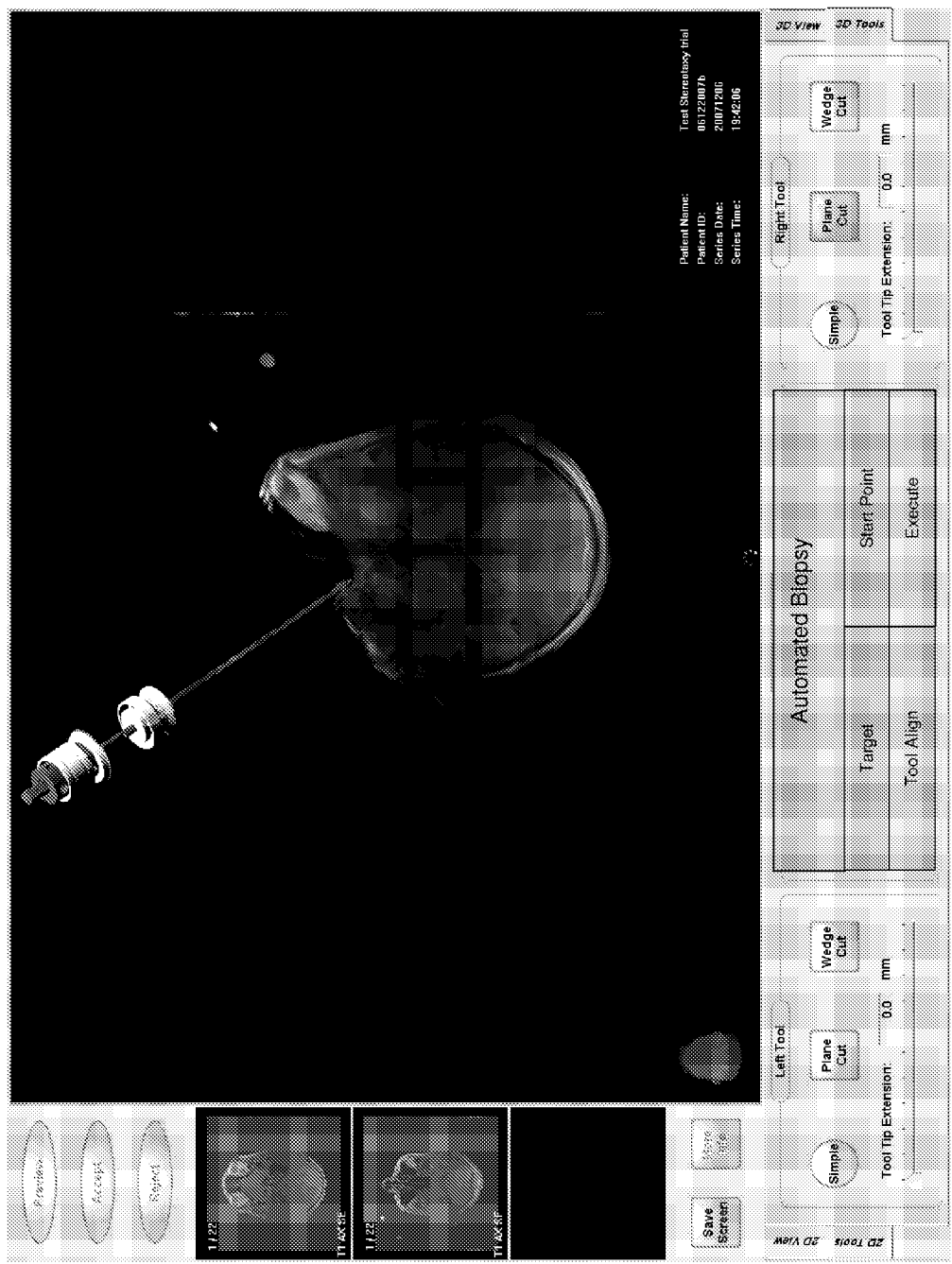
FIG. 12 shows the GUI of FIG. 11 in a 3D mode in which a representation of the tool chosen for use in the training/simulation is displayed at the relevant depth within a 3D image of a portion of the subject. The GUI reflects that a user has selected the "Plane Cut" option, which results in oblique slices being cut away on the head to the relevant tool tip depth.

In the version of MRID 402 shown in FIG. 12, the 3D Tools tab has been selected and the location of the tip of the tool relative to the subject's head is shown in 3D, where the 3D image is shown in this embodiment cut away on a plane that is normal to the axis along which the tool tip will travel, as a result of the selection of the "Plane Cut" button within the "Right Tool" box near the right of the screen. A user can manipulate the orientation of the 3D image through any suitable input device (e.g., a space ball) to move the displayed image and the overlaid tool so as to provide a desired view of the tissue affected by the proposed tool position and path. This overlay feature becomes available following the physical and MRI registration process and receipt of tool selection. Selection of the "Simple" button will replace the tool image with, for example, a thin red line of the same length as the tool so as not to obstruct the view of small structures. Selection of the "Wedge Cut" button will cut into the displayed 3D image at the location of the tool tip/extension line end by cutting away a wedge to reveal three orthogonal planes (e.g., sagittal, axial, coronal), where the tip of the tool/extension line end is at the juncture of the three planes. These cut-away options allow a user to evaluate the internal structure of the three-dimensional MR image to determine an optimal path of the relevant tool during a procedure.

An exemplary embodiment of one series of steps that can be used, following the registration procedure described above, to set up and execute a procedure (for example, an automated biopsy) is provided below. A user may first select a mode on the CSD, such as Stereotaxy Left Arm Mode, and then enable the left arm and power on the bore camera(s). The user may then choose the Simulation Mode on the CSD to disengage the left manipulator (which may, for example, be a left version of manipulator 100 from FIGS. 1C-3C or one of the manipulators shown in the '316 patent) from the motion of the relevant input device (such as input device 20). On the MRID, the user may then select the 2D Tools tab and the Track mode/function in the "Left Tool" box, causing the crosshairs to appear overlaying the relevant 2D image of the subject when the 2D mode is selected. A user may select a non-zero "Tool Tip Extension" value, using the slider bar, if a tool tip extension line is desired. If the Tool Tip Extension function is set greater than 0.0 mm, the crosshairs will track the location of the end of the extension line. If this parameter is set at zero, the tracking function will illustrate crosshairs on the 2D slice image at the location of the tip (distal end) of the tool. As the tool or extension line passes through the subject (e.g., the brain), subsequent 2D images (e.g., 2D slices) are shown. Likewise, if the tool or extension line is withdrawn from the subject, prior 2D slices are shown.

In this exemplary embodiment, the user can grasp the left input device and enable virtual or simulated motion of the tool by actuating (e.g., via use of the thumb) an enable button (e.g., button 29) on the input device. The user can then take the input device, and based on visual cues gained from toggling, as desired, between the 2D and 3D MRID views, move the virtual manipulator shown on the CSD and the manipulator's surgical tool to the area of the intended target. In certain embodiments, the CSD and the 2D and 3D MRID images can update in real time to show the location of the virtual (when in simulation mode) manipulator and its tool.

When the user has determined a desired target location, the user may disable the input device so that movement of the input device does not lead to further movement of the virtual manipulator and its tool. On either the 2D or 3D version of the MRID screen under "Automated Biopsy" (see, e.g., FIGS. 11 and 12), a user can then push "Target" to select the target location for the procedure, which is stored in terms of X, Y and Z Cartesian coordinates of the tool tip in image space (e.g., magnetic resonance imaging space), which is then transformed to robot space. These coordinates are registered as the tool tip if the extension line value equals zero, or as the end of the extension line if that value is greater than zero; as a result, a target location indicator will appear at the crosshairs location (for example, a red circle) in the 2D view and at the tool tip or extension line end location in the 3D view denoting the intended target.

A user can then enable the input device if it has been disabled (and in the same way that the input device was disabled) and cause the tool tip or extension line end to move toward the intended insertion point for the subject. A path indicator (for example, a green line) can then be visible in the 3D view that links the tip/extension line end to the selected target so that the user can see the trajectory and any tissue that will be penetrated or disturbed by the proposed tool tip path. The user may then move the input device to the desired entry point (which could be, for example, at the surface of the brain or head, or a small distance outside the head). If a burr hole has already been made, a user may ensure that the path goes through the burr hole without contacting the head. The user may then, but need not, disable the input device when the entry point and trajectory are acceptable.

A user may then push the button labeled "Start Point" on either the 2D or 3D version of the MRID and an indicator (e.g., a green circle) will appear at the crosshairs location in the 2D view and at the tool tip or extension line end location in the 3D view denoting the intended start point, which is stored in terms of X, Y and Z Cartesian coordinates of the tool tip in image space (e.g., magnetic resonance imaging space), which is then transformed to robot space. These coordinates are registered as the tool tip if the extension line value equals zero, or as the end of the extension line if that value is greater than zero. In this embodiment, the indicator will change in some way (e.g., the green line will turn red) to denote that the line (or path) is set, and the start point, termination point and trajectory (or path) will appear on the CSD. If a user desires to change the location of the Start Point or the Target, the user can use the input device to move the simulated tool tip/extension line to a new location and push the "Start Point" or "Target" button again in either the 2D or 3D version of the MRID. In certain embodiments, the system will ask the user to push the relevant button a second time to confirm replacement of the old point with a new point. After an acceptable trajectory is chosen, the user can exit the simulation mode on the CSD by designating that button again (e.g., by touching it on the screen again).

After selecting/determining the desired trajectory for the chosen tool, a user can execute the automated move by choosing the master/slave mode on the CSD, enabling the input device (e.g., by depressing button 29), and moving the input device to cause the manipulator (while watching the MRID and/or the bore camera or field camera image shown on display screen 403 shown in FIG. 4) to move to a location close to the start point selected for the movement and to be in an orientation that is as close to the selected trajectory as possible. The user may then disable the input device.

On the MRID, under "Automated Biopsy" in either the 2D or 3D view, the user can push the "Tool Align" button (see, e.g., FIGS. 11 and 12) and the manipulator will move to align with the programmed trajectory and place the tool tip at or near the selected start point (such as approximately two centimeters radially outward from the start point along the programmed trajectory). The user may then push the "Execute" button (under "Automated Biopsy"), and the user may be prompted to enable the input device to begin the automated movement (e.g., an automated biopsy).

The user may then grasp the input device and enable the system to begin the automated biopsy by enabling the input device in the same way it has been previously enabled (e.g., by pushing button 29). Taking this step causes the user to hold the input device in order for the procedure to take place. As a result of enabling the input device, the tool may move forward at a predetermined rate (which can be set in an initialization file) to the target location, at which point the surgical tool can perform a pre-programmed function, such as removing biopsy material. In certain embodiments in which the surgical tool is a biopsy tool equipped with two small sharpened scoops that open away from each other about axes that are normal to the longitudinal axis of the tool, the surgical tool's scoops will open, rotate 90 degrees clockwise, and close again, capturing tissue as a result. The surgical tool can then reverse direction straight out along the insertion trajectory.

Figure 13:
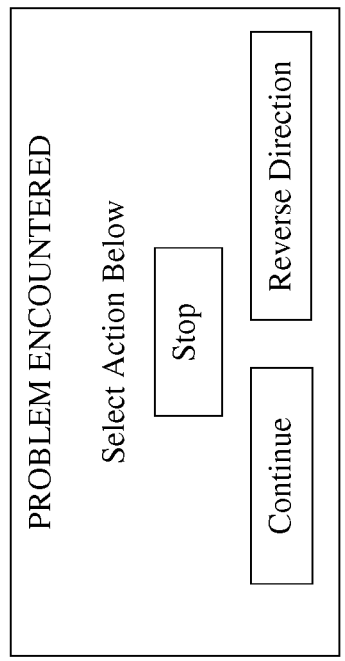
FIG. 13 shows a warning box that can appear on a GUI such as the one in FIG. 5 if a problem is encountered during an automated procedure.

If a problem is encountered during execution of the automated move, the user can disable the input device (e.g., by depressing button 29) to stop the move. The CSD will then present the user with a selection box, such as the one shown in FIG. 13, that includes options to stop, continue, and reverse direction. Once a selection is chosen, the tool will move again when the user enables the input device.

In addition to providing a single axis lock for movement of a given surgical tool during any procedure, embodiments of the present methods, devices, and systems may therefore also allow a user (e.g., a surgeon) to simulate multiple paths for a surgical tool prior to conducting the actual surgical procedure, evaluate those paths for the tissue they may affect, and choose a desired path by selecting a target point and a start point. The present devices and systems are configured to limit (electronically) the tool to a linear path; as a result, only a start point and a target point are needed to determine the tool path. Embodiments of the present devices and system may also comprise multiple safety features to allow the user to maintain control of the tool.

Embodiments of the present methods may be coded as software stored on any suitable computer readable media (e.g., tangible computer readable media), such as any suitable form of memory or data storage device, including but not limited to hard drive media, optical media, RAM, SRAM, DRAM, SDRAM, ROM, EPROM, EEPROM, tape media, cartridge media, flash memory, memory stick, and/or the like. Tangible computer readable media includes any physical medium that can store or transfer information. Such embodiments may be characterized as tangible computer readable media having (or encoded with) computer executable (e.g., machine readable) instructions for performing certain step(s). The term "tangible computer readable medium" does not include wireless transmission media, such as carrier waves. The term "computer readable medium," however, does cover wireless transmission media, and some embodiments of the present methods may include wireless transmission media carrying the computer readable instructions described above. The software can be written according to any technique known in the art. For instance, the software may be written in any one or more computer languages (e.g., ASSEMBLY, PASCAL, FORTRAN, BASIC, C, C++, C#, JAVA, Perl, Python) or using scientific packages like, but not limited to, Matlab®, R, S-Plus®, and SAS®. The code may be to enable it to be compiled on all common platforms (e.g., Microsoft®, Linux®, Apple Macintosh® OS X, Unix®). Further, well-established cross-platform libraries such as OpenGL® may be utilized to execute embodiments of the present methods, devices and systems. Multi-threading may be used wherever applicable to reduce computing time on modern single- and multi-processor based hardware platforms. As discussed above and illustrated in the figures, the software may include a GUI, which may provide a user with a more intuitive feel when running the software. Different fields may be accessible by screen touching, a mouse and/or keyboard. Alarms, cues, and the like may be done via pop-up windows, audible alerts, or any other techniques known in the art.

Some (up to all) of the steps described in the sections above may be implemented using a computer having a processor (e.g., one or more integrated circuits) programmed with firmware and/or running software. Some (up to all) of the steps described in the sections above may be implemented using a distributed computing environment, which is one example of a computer system. In a distributed computing environment, multiple computers may be used, such as those connected by any suitable number of connection mediums (e.g., a local area network (LAN), a wide area network (WAN), or other computer networks, including but not limited to Ethernets, enterprise-wide computer networks, intranets and the Internet, and the connections between computers can be wired or wireless). Servers and user terminals can be part of a given computer system. Furthermore, embodiments of suitable computer systems may be implemented on application specific integrated circuits (ASICs) or very large scale integrated (VLSI) circuits, and further (or alternatively) may be configured to use virtualization of resources, virtual computing, and/or cloud computing to achieve the specified functions. In fact, persons of ordinary skill in the art may utilize any number of suitable structures capable of executing logical operations in order to achieve the functions described above in a computer system consistent with this disclosure.

Descriptions of well known processing techniques, components and equipment have been omitted so as not to unnecessarily obscure the present methods, devices and systems in unnecessary detail. The descriptions of the present methods, devices and systems are exemplary and non-limiting. Certain substitutions, modifications, additions and/or rearrangements falling within the scope of the claims, but not explicitly listed in this disclosure, may become apparent to those of ordinary skill in the art based on this disclosure. For example, while one MRID is disclosed that allows a user to toggle between the display of 2D and 3D images, in alternative embodiments two separate display screens may be used for 2D and 3D images, respectively. As another example, while an automated movement for a biopsy of brain tissue has been described above as an example of a suitable movement that can be pre-programmed according to the techniques disclosed above, there are many other surgical and/or diagnostic movements that can be automated using the present techniques, including breast biopsies, the implantation of drugs, the implantation of electrodes (e.g., for epilepsy), the implantation of stem cells, and the drilling of bone spurs from vertebrae without line of sight, among others. Furthermore, it will be appreciated that in the development of a working embodiment, numerous implementation-specific decisions must be made to achieve the developers' specific goals, such as compliance with system-related and business-related constraints, which will vary from one implementation to another. While such a development effort might be complex and time-consuming, it would nonetheless be a routine undertaking for those of ordinary skill in the art having the benefit of this disclosure.

The appended claims are not to be interpreted as including means-plus-function limitations, unless such a limitation is explicitly recited in a given claim using the phrase(s) "means for" and/or "step for," respectively.

The invention claimed is:

1. A computer system configured to perform at least the following functions:
   receive a command to restrict movement of a tool operatively associated with a robotic arm along a single axis, the robotic arm being configured for use in surgery;
   receive a first dataset defining a first position and first orientation of an input device, the input device being disengageably linked with the robotic arm through a master-slave relationship in which the input device is the master;
   receive a second dataset defining a second position and second orientation of the input device;
   determine a component of the difference between the first position and first orientation of the input device and the second position and second orientation of the input device along one axis, the one axis related by a transformation to the single axis; and
   send one or more signals to effect a move of the tool, the move effected using the component and the transformation, whereby the move is restricted to along the single axis.

2. The computer system of claim 1, further configured to perform at least the following:
   receive data sufficient to enable determination of a position of a portion of the tool and an orientation of the tool, the tool having a longitudinal axis, wherein the single axis of is defined relative to the longitudinal axis of the tool; and
   receive a move command to move the tool;
   wherein the one or more signals to effect the move of the tool are sent in response to the move command.

3. The computer system of claim 1, wherein the computer system is useful in simulating, planning and/or executing an automated surgical procedure, and wherein the computer system is further configured to perform at least the following functions:
   receive data designating a target location for the tool based on the first dataset;
   receive data designating a second location for the tool based on the second dataset; and
   receive an automate command to begin an automated movement of the tool, wherein the one or more signals are sent in response to the automate command and the move effected is the automated movement of the tool, and wherein the single axis along which the tool moves is defined by the second location and the target location.

4. The computer system of claim 3, further configured to receive engagement data indicating the input device has been engaged with or disengaged from the robotic arm and wherein the move occurs only if the engagement data received indicates the input device is engaged with the robotic arm.

5. The computer system of claim 3, further configured to perform at least the following function:
   cause manipulation of the tool at the target location.

6. The computer system of claim 3, further configured to perform at least the following functions:
   display a simulated representation of the tool;
   display a three-dimensional representation of a portion of a subject;
   prior to receiving the data designating the second location, display a trajectory planning line extending from the target location to a tip of the simulated representation of the tool overlaid on the three-dimensional representation of the portion of the subject; and
   move the trajectory planning line in response to input from an input device linked to the simulated representation of the tool.

7. The computer system of claim 6, further configured to perform at least the following function:
   display in addition to the simulated representation of the tool, an indicator showing a path from the second location to the target location.

8. A computer readable medium having stored thereon machine readable instructions for performing at least the functions of claim 3.

9. The computer system of claim 3, wherein the one or more signals sent in response to the automate command effect the automated movement at a pre-determined rate, which is distinct from a real-time response to manipulation of the input device.

10. The computer system of claim 3, wherein the computer system is further configured to receive a command to stop the automated movement before the automated movement is complete.

11. The computer system of claim 3, further configured to perform at least the following functions:
   display a simulated representation of the robotic arm;
   display a simulated representation of the tool;

receive a command to operate in a simulation mode, wherein in simulation mode the input device can be reversibly linked to the simulated representation of the robotic arm;

display a first two-dimensional (2D) image of a portion of a subject;

display an indicator of the target location overlaid on the 2D image;

move the indicator of the target location in response to input from the input device, wherein the input device is linked to the simulated representation of the tool;

display a three-dimensional (3D) representation of a portion of the subject having the simulated representation of the tool overlaid on the 3D representation such that a tip of the tool or a line extending from the tool is shown in the same relative location as the indicator of the target location;

move the tip of the tool or the line in response to the input from the input device; and alter the 3D representation in response to the input from the input device.

12. The computer system of claim 11, further configured to display a second 2D image of a portion of the subject.

13. The computer system of claim 1, wherein determining the component of the difference along the one axis comprises determining a delta value between the first dataset and the second dataset in the one axis, and wherein the computer system is further configured to perform the following function:

determine a corresponding delta value for the tool in the single axis based on the delta value in the one axis.

14. The computer system of claim 13, wherein determining the corresponding delta value comprises zeroing all non-single axis parameters received from the input device.

15. The computer system of claim 13, wherein determining the corresponding delta value comprises determining delta values in more than one axis and selecting, from these delta values, the corresponding delta value in the single axis.

* * * * *

UNITED STATES PATENT AND TRADEMARK OFFICE
CERTIFICATE OF CORRECTION

| | | |
|---|---|---|
| PATENT NO. | : 8,560,118 B2 | Page 1 of 1 |
| APPLICATION NO. | : 12/596426 | |
| DATED | : October 15, 2013 | |
| INVENTOR(S) | : Greer et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 898 days.

Signed and Sealed this
Third Day of March, 2015

Michelle K. Lee
*Deputy Director of the United States Patent and Trademark Office*